(12) United States Patent
Harmer et al.

(10) Patent No.: US 6,809,218 B2
(45) Date of Patent: Oct. 26, 2004

(54) SOL-GEL DERIVED POROUS MICROCOMPOSITE OF PERFLUORINATED ION-EXCHANGE POLYMER AND METAL OXIDE

(75) Inventors: Mark Andrew Harmer, Wilmington, DE (US); Qun Sun, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 10/680,337

(22) Filed: Oct. 7, 2003

(65) Prior Publication Data

US 2004/0072672 A1 Apr. 15, 2004

Related U.S. Application Data

(60) Division of application No. 10/322,786, filed on Dec. 18, 2002, now Pat. No. 6,680,406, which is a division of application No. 09/670,530, filed on Sep. 27, 2000, now Pat. No. 6,515,190, which is a division of application No. 09/324,931, filed on Jun. 3, 1999, now Pat. No. 6,160,190, which is a division of application No. 09/121,106, filed on Jul. 23, 1998, now Pat. No. 5,948,946, which is a division of application No. 08/574,751, filed on Dec. 19, 1995, now Pat. No. 5,824,622, which is a continuation-in-part of application No. 08/362,063, filed on Dec. 22, 1994, now abandoned, which is a continuation-in-part of application No. 08/180,250, filed on Jan. 12, 1994, now abandoned.

(30) Foreign Application Priority Data

Jan. 10, 1995 (US) .................... PCT/US95/00012

(51) Int. Cl.⁷ .................... C07C 67/04; C07C 67/00; C07C 67/05
(52) U.S. Cl. .................... 560/247; 560/241; 560/243
(58) Field of Search .................... 560/241, 243, 560/247

(56) References Cited

U.S. PATENT DOCUMENTS

| | | | |
|---|---|---|---|
| 3,506,635 A | 4/1970 | Anderson | |
| 4,038,213 A | 7/1977 | McClure et al. | |
| 4,041,090 A | 8/1977 | McClure | |
| 4,056,578 A | 11/1977 | McClure et al. | |
| 4,065,515 A | 12/1977 | McClure et al. | |
| 4,275,228 A | * 6/1981 | Gruffaz et al. | .............. 560/247 |
| 4,414,409 A | 11/1983 | Waller | |
| 4,433,082 A | 2/1984 | Grot | |
| 4,791,081 A | 12/1988 | Childress et al. | |
| 5,086,085 A | 2/1992 | Pekala | |
| 5,094,995 A | 3/1992 | Butt et al. | |
| 5,252,654 A | 10/1993 | David et al. | |

FOREIGN PATENT DOCUMENTS

| | | |
|---|---|---|
| EP | 0288295 | 10/1988 |
| EP | 0324080 | 7/1989 |
| EP | 0338309 | 10/1989 |
| EP | 0503688 | 9/1992 |
| EP | 0367408 | 5/1999 |
| FR | 1248426 | 12/1960 |
| GB | 2238539 A | * 11/1989 |

OTHER PUBLICATIONS

Mauritz, K. A. et al., Polym. Mater. Sci. Eng., 58, 1079–1082, 1988.

Olah, G. A. et al., Synthesis, 513–531, 1986.

Waller, F. J. Catal. Rev.–Sci. Eng., 1–12, 1986.

Weaver, J.D. et al., Catalysis Today, 14, 195–210, 1992.

Mauritz, K.A. et al., Multiphase Polymers: Blends and Ionomers, American Chemical Society, 401–417, Chapter 16, 1989.

Waller, F. J. et al. Chemtech, 438–441 (Jul. 1987).

Waller, F. J., In Polymeric Reagents and Catalysts, Ford, W.T. (Ed.), Chap. 3, ACS Symposium Series 308, ACS, Washington, DC (1986).

Martin, C.R. et al., Anal. Chem. 54, 1639–1641 (1982).

* cited by examiner

*Primary Examiner*—J. Parsa

(57) ABSTRACT

Porous microcomposites have been prepared from perfluorinated ion-exchange polymer and metal oxides such as silica using the sol-gel process. Such microcomposites possess high surface area and exhibit extremely high catalytic activity.

6 Claims, 1 Drawing Sheet

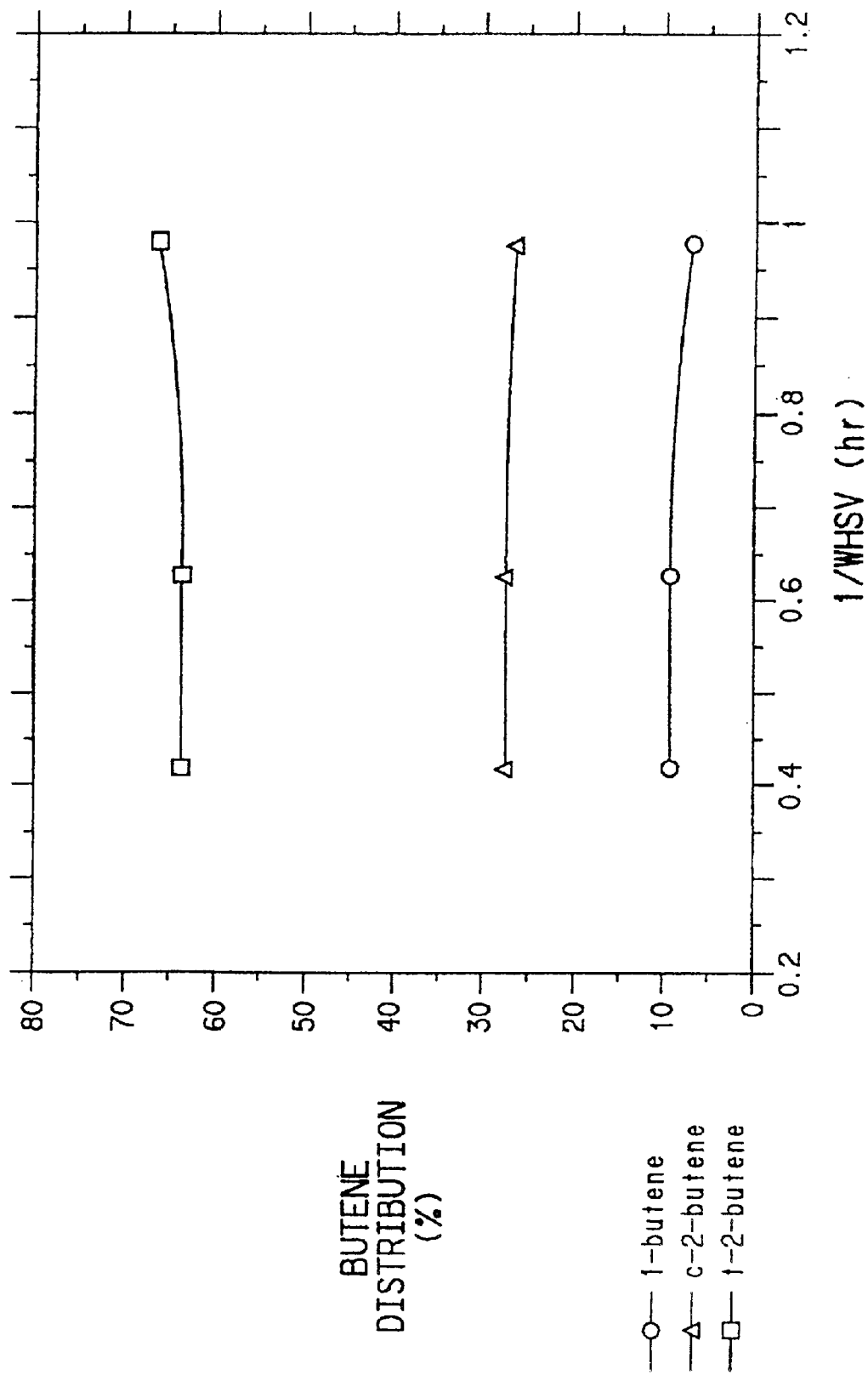

SOL-GEL DERIVED POROUS MICROCOMPOSITE OF PERFLUORINATED ION-EXCHANGE POLYMER AND METAL OXIDE

CROSS REFERENCE TO RELATED APPLICATIONS

This application is a divisional of Application Ser. No. 10/322,786, filed Dec. 18, 2002, now U.S. Pat. No. 6,680,406, which is a divisional of Application Ser. No. 09/670,530, filed Sep. 27, 2000, now U.S. Pat. No. 6,515,190, which is a divisional of Application Ser. No. 09/324,931, filed Jun. 3, 1999, now U.S. Pat. No. 6,160,190, which is a divisional of Application Ser. No. 09/121,106 filed Jul. 23,1998, now U.S. Pat. No. 5,948,946, which is a divisional of Application Ser. No. 08/574,751 filed Dec. 19,1995, now U.S. Pat. No. 5,824,622, which is a continuation-in-part of Application Ser. No. 08/362,063 filed Dec. 22,1994, now abandoned, which is a continuation-in-part of Application Ser. No. 08/180,250 filed Jan. 12, 1994, now abandoned.

FIELD OF THE INVENTION

This invention relates to porous microcomposites comprising perfluorinated ion-exchange polymers (PFIEP) containing pendant sulfonic acid groups and/or pendant carboxylic acid groups entrapped within and highly dispersed throughout a metal oxide network, prepared using a sol-gel process. Due to their high surface area and acid functionality these microcomposites possess wide utility as improved solid acid catalysts.

TECHNICAL BACKGROUND

U.S. Pat. No. 5,252,654 discloses polymeric composites comprising an interpenetrating network of an organic polymer and an inorganic glassy polymer and a process for making such composites. The disclosed material is nonporous, and the use of perfluorinated ion-exchange polymers (PFIEP) containing pendant sulfonic acid groups or pendant carboxylic acid groups is not disclosed.

K. A. Mauritz et al., Polym. Mater. Sci. Eng. 58, 1079–1082(1988), in an article titled "Nafion-based Microcomposites: Silicon Oxide-filled Membranes", discuss the formation of micro composite membranes by the growth of silicon oxide microclusters or continuous silicon oxide interpenetrating networks in pre-swollen "NAFION®" sulfonic acid films. "NAFION®" is a registered trademark of E. I. du Pont de Nemours and Company.

U.S. Pat. No. 5,094,995 discloses catalysts comprising perfluorinated ion-exchange polymers (PFIEP) containing pendant sulfonic acid groups supported on an inert carrier having a hydrophobic surface comprising calcined shot coke.

U.S. Pat. No. 4,038,213 discloses the preparation of catalysts comprising perfluorinated ion-exchange polymers (PFIEP) containing pendant sulfonic acid groups on a variety of supports.

The catalytic utility of perfluorinated ion-exchange polymers (PFIEP) containing pendant sulfonic acid groups, supported and unsupported has been broadly reviewed: G. A. Olah et al., Synthesis, 513–531(1986) and F. J. Waller, Catal. Rev.-Sci. Eng., 1–12(1986).

SUMMARY OF THE INVENTION

This invention provides a porous microcomposite comprising perfluorinated ion-exchange polymer containing pendant sulfonic and/or carboxylic acid groups entrapped within and highly dispersed throughout a network of metal oxide, wherein the weight percentage of perfluorinated ion-exchange polymer in the microcomposite is from about 0.1 to 90 percent, preferably from about 5 to about 80 percent, and wherein the size of the pores in the microcomposite is about 0.5 nm to about 75 nm.

In a separate embodiment, the microcomposite can simultaneously contain larger pores ranging from about 75 nm to about 1000 nm, wherein these larger pores are formed by introducing acid-extractable filler particles during the formation process.

This invention further provides the process of preparation of a porous microcomposite which comprises perfluorinated ion-exchange polymer containing pendant sulfonic and/or carboxylic acid groups entrapped within and highly dispersed throughout a network of metal oxide, wherein the weight percentage of perfluorinated ion-exchange polymer in the microcomposite is from about 0.1 to 90 percent, and wherein the size of the pores in the microcomposite is about 0.5 nm to about 75 nm;

said process comprising the steps of:
  a. mixing the perfluorinated ion-exchange polymer with one or more metal oxide precursors in a common solvent;
  b. initiating gelation;
  c. allowing sufficient time for gelation and aging of the mixture; and
  d. removing the solvent.

In a further preferred embodiment the process further comprises at step (a), adding to the mixture an amount from about 1 to 80 weight percent of an acid extractable filler particle, after d;
  e. acidifying the product of step d by the addition of acid; and
  f. removing the excess acid from the microcomposite;
  to yield a microcomposite further containing pores in the range of about 75 nm to about 1000 nm.

The present invention also provides an improved process for the nitration of an aromatic compound wherein the improvement comprises contacting said aromatic compound with a catalytic microcomposite of the present invention, described above.

The present invention further provides an improved process for the esterification of a carboxylic acid with an olefin wherein the improvement comprises contacting said carboxylic acid with a catalytic microcomposite of the present invention, described above.

The present invention also provides an improved process for the polymerization of tetrahydrofuran wherein the improvement comprises contacting said tetrahydrofuran with a catalytic microcomposite of the present invention, described above.

The present invention further provides an improved process for the alkylation of an aromatic compound with an olefin wherein the improvement comprises contacting said aromatic compound with a catalytic microcomposite of the present invention, described above.

The present invention provides an improved process for the acylation of an aromatic compound with an acyl halide wherein the improvement comprises contacting said aromatic compound with a catalytic microcomposite of the present invention, described above.

The present invention further provides an improved process for the dimerization of an alpha substituted styrene, wherein the improvement comprises contacting said alpha substituted styrene with a catalytic microcomposite of the present invention, described above.

The present invention further provides a process for regenerating a catalyst comprising a microcomposite of the present invention, as described above, comprising the steps of: mixing the microcomposite with an acid, and removing the excess acid.

The present invention also provides a process for the isomerization of an olefin comprising contacting said olefin at isomerization conditions with a catalytic amount of a porous microcomposite, said microcomposite comprising perfluorinated ion-exchange polymer containing pendant sulfonic and/or carboxylic acid groups entrapped within and highly dispersed throughout a network of metal oxide, wherein the weight percentage of perfluorinated ion-exchange polymer in the microcomposite is from about 0.1 to 90 percent, preferably from about 5 to about 80 percent, most preferably from about 5 to about 20 percent and wherein the size of the pores in the microcomposite is about 0.5 nm to about 75 nm.

BRIEF DESCRIPTION OF THE DRAWINGS

FIG. 1 is a graph showing data from Example 58 and Table 4b which shows the effect of contact time at 50° C. and He/1-butene=1.2/1.0 on 1-butene isomerization over a 13 wt % "NAFION®" PFIEP/silica microcomposite prepared as in Example 16.

DETAILED DESCRIPTION OF THE INVENTION

The organic-inorganic polymer microcomposites of the present invention are high surface area, porous microcompositions which exhibit excellent catalytic activity. Whereas the surface area of "NAFION®" NR 50 PFIEP, a commercial product, is approximately 0.02 m² per gram, a preferred embodiment of the present invention comprises microcomposites of PFIEP and silica having a surface area typically of 5 to 500 m² per gram. The composition of the present invention exists as a particulate solid which is porous and glass-like in nature, typically 0.1–4 mm in size and structurally hard, similar to dried silica gels. The perfluorinated ion exchange polymer (PFIEP) is highly dispersed within and throughout the silica network of the microcomposite of the present invention, and the microstructure is very porous. The porous nature of this material is evident from the high surface areas measured for these glass-like pieces, having typical pore diameters in the range of 1–25 nm. Another preferred embodiment is the use of the present invention in pulverized form.

In another preferred embodiment, macroporosity (pore sizes about 75 to about 1000 nm) is also introduced into the microcomposite, resulting in a microcomposite having both increased surface area from the micropores and mesopres (0.5–75 nm) and enhanced accessibility resulting from the macropores (75–1000 nm).

Perfluorinated ion-exchange polymers (PFIEP) containing pendant sulfonic acid, carboxylic acid, or sulfonic acid and carboxylic acid groups used in the present invention are well known compounds. See, for example, Waller et al., Chemtech, July, 1987, pp. 438–441, and references therein, and U.S. Pat. No. 5,094,995, incorporated herein by reference. Perfluorinated ion-exchange polymers (PFIEP) containing pendant carboxylic acid groups have been described in U.S. Pat. No. 3,506,635, which is also incorporated by reference herein. Polymers discussed by J. D. Weaver et al., in Catalysis Today, 14 (1992) 195–210, are also useful in the present invention. Polymers that are suitable for use in the present invention have structures that include a substantially fluorinated carbon chain that may have attached to it side chains that are substantially fluorinated. In addition, these polymers contain sulfonic acid groups or derivatives of sulfonic acid groups, carboxylic acid groups or derivatives of carboxylic acid groups and/or mixtures of these groups. For example, copolymers of a first fluorinated vinyl monomer and a second fluorinated vinyl monomer having a pendant cation exchange group or a pendant cation exchange group precursor can be used, e.g., sulfonyl fluoride groups ($SO_2F$) which can be subsequently hydrolyzed to sulfonic acid groups. Possible first monomers include tetrafluoroethylene (TFE), hexafluoropropylene, vinyl fluoride, vinylidine fluoride, trifluoroethylene, chlorotrifluoroethylene, perfluoro (alkyl vinyl ether), and mixtures thereof. Possible second monomers include a variety of fluorinated vinyl ethers with pendant cation exchange groups or precursor groups. Preferably, the polymer contains a sufficient number of acid groups to give an equivalent weight of from about 500 to 20,000, and most preferably from 800 to 2000. Representative of the perfluorinated polymers for use in the present invention are "NAFION®" PFIEP (a family of polymers for use in the manufacture of industrial chemicals, commercially available from E. I. du Pont de Nemours and Company), and polymers, or derivatives of polymers, disclosed in U.S. Pat. Nos. 3,282,875; 4,329,435; 4,330,654; 4,358,545; 4,417,969; 4,610,762; 4,433,082; and 5,094,995. More preferably the polymer comprises a perfluorocarbon backbone and a pendant group represented by the formula —$OCF_2CF(CF_3)OCF_2CF_2SO_3X$, wherein X is H, an alkali metal or $NH_4$. Polymers of this type are disclosed in U.S. Pat. No. 3,282,875.

Typically, suitable perfluorinated polymers are derived from sulfonyl group-containing polymers having a fluorinated hydrocarbon backbone chain to which are attached the functional groups or pendant side chains which in turn carry the functional groups. Fluorocarbosulfonic acid catalysts polymers useful in preparing the microcomposites of the present invention have been made by Dow Chemical and are described in Catalyis Today, 14 (1992) 195–210. Other perfluorinated polymer sulfonic acid catalysts are described in Synthesis, G. I. Olah, P. S. Iyer, G. K. Surya Prakash, 513–531 (1986).

There are also several additional classes of polymer catalysts associated with metal cation ion-exchange polymers and useful in preparing the microcomposite of the present invention. These comprise 1) a partially cation-exchanged polymer, 2) a completely cation-exchanged polymer, and 3) a cation-exchanged polymer where the metal cation is coordinated to another ligand (see U.S. Pat. No. 4,414,409, and Waller, F. J. In Polymeric Reagents and Catalysts; Ford, W. T., Ed.,; ACS Symposium Series 308; American Chemical Society; Washington, D.C., 1986, Chapter 3).

Preferred PFIEP suitable for use in the present invention comprise those containing sulfonic acid groups. Most preferred is a sulfonated "NAFION®" PFIEP.

Perfluorinated ion-exchange polymers are used within the context of the invention in solution form. It is possible to dissolve the polymer by heating it with an aqueous alcohol to about 240° C. or higher for several hours in a high pressure autoclave (see U.S. Pat. No. 4,433,082 or Martin et al., Anal. Chem., Vol. 54, pp 1639–1641 (1982). Other solvents and mixtures may also be effective in dissolving the polymer.

Ordinarily, for each part by weight of polymer employed to be dissolved, from as little as about 4 or 5 parts by weight up to about 100 parts by weight, preferably 20–50 parts by weight, of the solvent mixture are employed. In the preparation of the dissolved polymer, there is an interaction between the equivalent weight of the polymer employed, the temperature of the process, and the amount and nature of the solvent mixture employed. For higher equivalent weight polymers, the temperature employed is ordinarily higher and the amount of liquid mixture employed is usually greater.

The resulting mixture can be used directly and may be filtered through fine filters (e.g., 4–5.5 micrometers) to obtain clear, though perhaps slightly colored, solutions. The mixtures obtained by this process can be further modified by removing a portion of the water, alcohols and volatile organic by-products by distillation.

Commercially available solutions of perfluorinated ion-exchange polymers can also be used in the preparation of the microcomposite of the present invention (e.g., at 5 wt % solution of a perfluorinated ion-exchange powder in a mixture of lower aliphatic alcohols and water, Cat. No. 27,470-4, Aldrich Chemical Company, Inc., 940 West Saint Paul Avenue, Milwaukee, Wis. 53233).

"Metal oxide" signifies metallic or semimetallic oxide compounds, including, for example, alumina, silica, titania, germania, zirconia, aluminosilicates, zirconyl-silicates, chromic oxides, germanium oxides, copper oxides, molybdenum oxides, tantalum oxides, zinc oxides, yttrium oxides, vanadium oxides, and iron oxides. Silica is most preferred. The term "metal oxide precursor" refers to the form of the metal oxide which is originally added in the sol-gel process to finally yield a metal oxide in the final microcomposite. In the case of silica, for example, it is well known that a range of silicon alkoxides can be hydrolyzed and condensed to form a silica network. Such precursors as tetramethoxysilane (tetramethyl orthosilicate), tetraethoxysilane (tetraethyl orthosilicate), tetrapropoxysilane, tetrabutoxysilane, and any compounds under the class of metal alkoxides which in the case of silicon is represented by $Si(OR)_4$, where R includes methyl, ethyl, n-propyl, iso-propyl, n-butyl, sec-butyl, iso-butyl, tert-butyl or where R is a range of organic groups, such as alkyl. Also included as a precursor form is silicon tetrachloride. Further precursor forms comprise organically modified silica, for example, $CH_3Si(OCH_3)_3$, $PhSi(OCH_3)_3$, and $(CH_3)_2Si(OCH_3)_2$. Other network formers include metal silicates, for example, potassium silicate, sodium silicate, lithium silicate. K, Na or Li ions can be removed using a DOWEX® cation exchange resin (sold by Dow Chemical, Midland, Mich., which generates polysilicic acid which gels at slightly acid to basic pH. The use of "LUDOX®" colloidal silica (E. I. du Pont de Nemours and Company, Wilmington, Del.) and fumed silica ("CAB-O-SIL®" sold by Cabot Corporation of Boston, Mass.) which can be gelled by altering pH and adjusting the concentration in solution will also yield a metal oxide network in the microcomposite of the invention. For example, typical precursor forms of silica are $Si(OCH_3)_4$, $Si(OC_2H_5)_4$ and $Na_2SiO_3$; and a typical precursor form of alumina is aluminum tri-secbutoxide $Al(OC_4H_9)_3$.

"Acid extractable filler particles" which are used in the process of the invention to introduce macropores of about 75 to about 1000 nm into the microcomposite include particles which are insoluble in the preparative gel-forming solvent, but are acid soluble and extractable from the formed microcomposite. Such filler particles include, for example, alkali metal carbonates or alkaline earth carbonates, such as calcium carbonate, sodium carbonate and potassium carbonate.

The first stage of the process for the preparation of the microcomposite of the present invention involves preparing a gel solution that contains both the perfluorinated ion-exchange polymer (PFIEP) containing pendant sulfonic acid groups and/or pendant carboxylic acid groups and one or more metal oxide precursors in a common solvent.

This solvent normally comprises water and various lower aliphatic alcohols such as methanol, 1-propanol, 2-propanol, mixed ethers and n-butanol. Thus, in some cases the water necessary for gel formation can be supplied by the water in the reaction solvent. Other polar solvents which may be suitable for the particular metal oxide precursor/polymer selected include acetonitrile, dimethyl formamide, dimethylsulfoxide, nitromethane, tetrahydrofuran and acetone. Toluene, alkanes and fluorocarbon-containing solvents can also be useful in some instances to solubilize the polymer.

Gelation may in some instances self-initiate, for example, when water is present in the common solvent, or via rapid drying, such as spray drying. In other instances, gelation must be initiated, which can be achieved in a number of ways depending on the initial mixture of polymer, metal oxide precursor and solvent selected. Gelation is dependent on a number of factors such as the amount of water present, because water is required for the hydrolysis and condensation reaction. Other factors include temperature, solvent type, concentrations, pH, pressure and the nature of the acid or base used. The pH can be achieved in a number of ways, for example, by adding base to the PFIEP solution or by adding the PFIEP solution to the base, or by adding the metal oxide to the solution than adjusting pH with acid or base. Another variable in addition to the mode of addition for achievement of pH is the concentration of base employed. Gels can also be formed by acid catalyzed gellation. See Sol-Gel Science, Brinker, C. J. and Scherer, G. W., Academic Press, 1990. Non-gelled PFIEP/metal oxide solution may be spray dried to yield dried PFIEP/metal oxide composites.

Time required for the gel forming reaction can vary widely depending on factors such as acidity, temperature, and concentration. It can vary from practically instantaneous to several days.

The gel forming reaction can be carried out at virtually any temperature at which the solvent is in liquid form. The reaction is typically carried out at room temperature.

Pressure over the gel forming reaction is not critical and may vary widely. Typically the reaction is carried out at atmospheric pressure. The gel forming reaction can be carried out over a wide range of acidity and basicity depending upon the amount of base added to the gel precursor.

After formation, but before isolation, the gel, still in the presence of its reaction solvent, may be allowed to stand for a period of time. This is referred to as aging.

The product is dried at room temperature or at elevated temperatures in an oven for a time sufficient to remove solvent. Drying can be done under vacuum, or in air or using an inert gas such as nitrogen. Optionally, after aging and/or removal of the solvent, the hard glass-like product can be ground and passed through a screen, preferably a 10-mesh screen. Grinding generates smaller particles (and greater surface area) which are more readily re-acidified. Grinding is especially useful for microcomposites having a high weight percent of PFIEP.

Preferably, following removal of the solvent and optional grinding, the material is reacidified, washed and filtered. This may be repeated a number of times. Reacidification of the material converts, for example, the sodium salt of the perfluorosulfonic acid into the acidic, active form. Suitable acids comprise HCl, $H_2SO_4$ and nitric acid.

A number of reaction variables, for example acidity, basicity, temperature, aging, method of drying and drying time of gels, have been found to affect the pore size and pore size distribution. Both higher pH and longer aging of gels (before solvent removal) lead to larger final pore size in the dried PFIEP/metal oxide gels. Pore size can be varied over a wide range (about 0.5 to about 75 nm) depending on the variables described above. Aging of the wet gels (in the presence of the solvent) for a few hours at 75° C. also leads to an increase in pore size although over a smaller range. This effect is characteristic of silica type gels, where the aging effect gives rise to an increasingly cross linked network which upon drying is more resistant to shrinkage and thus a higher pore size results. See, for example, the text Sol-Gel Science, Brinker, C. J. and Scherer, G. W., Academic Press, 1990, pp. 518–523. In the present invention, preferred, pore size is about about 0.1 nm to about 75 nm, more preferred about 0.5 to about 50 nm, most preferred is about 0.5 to about 30 nm.

Microcomposites comprising macropores (about 75 to about 1000 nm) have also been developed hereunder which have both high surface area and micro-, meso- and macroporosity. Such a structure is easily accessible for catalytic and ion exchange purposes. This unique microstructure of the present invention is prepared by adding sub-micron size particles of calcium carbonate to a PFIEP/metal oxide precursor solution prior to the gelation step. Upon acidification of the glass gels, the calcium carbonate dissolves out leaving large (about 500 nm) pores connected throughout the matrix with a sub-structure of about 10 nm micropores. This kind of structure offers a high surface area PFIEP/metal oxide network within the microcomposite which is readily accessible throughout. Macroporosity can be achieved by adding approximately 1 to 80 wt % (based upon gel weight) of acid-extractable filler particles such as calcium carbonate, to the sol-gel process prior to the gelation step.

It is believed that the highly porous structure of the microcomposites of the present invention consists of a continuous metal oxide phase which entraps a highly dispersed PFIEP within and throughout a connected network of porous channels. The porous nature of the material can be readily demonstrated, for example, by solvent absorption. The microcomposite can be observed to emit bubbles which are evolved due to the displacement of the air from within the porous network.

The distribution of the PFIEP entrapped within and throughout the metal oxide is on a very fine sub-micron scale. The distribution can be investigated using electron microscopy, with energy dispersive X-ray analysis, which provides for the analysis of the elements Si and O (when using silica, for example) and C and F from the PFIEP fluoropolymer. Fractured surfaces within a particle and several different particles for compositions ranging from 10 to 40 wt % "NAFION®" PFIEP were analyzed, and all of the regions investigated showed the presence of both the silica and PFIEP polymer from the edge to the center of the microcomposite particles; thus the microcomposite exhibited an intimate mixture of Si and F. No areas enriched in entirely Si or entirely F were observed, rather a uniform distribution of Si and F was seen. This bicomponent description is believed to be accurate for areas as low 0.1 micrometer in size. The morphology of the microcomposites, as prepared by Example 1, is somewhat particulate in nature, again as observed using scanning electron microscopy. This is typical of silica gel type material prepared using this sol-gel procedure. The primary particle size is on the order of 5–10 nm. This was also confirmed using small angle x-ray scattering experiments on the material, which revealed a domain size in the range of 5–10 nm. The data is consistent with the PFIEP being entrapped within and highly dispersed throughout the silica.

The microcomposites of the invention are useful as ion exchange resins, and as catalysts, for example, for alkylating aliphatic or aromatic hydrocarbons, for decomposing organic hydroperoxides, such as cumene hydroperoxide, for sulfonating or nitrating organic compounds, and for oxyalkylating hydroxylic compounds. A serious drawback to the commercial use of previous perfluorocarbon sulfonic acid catalysts has been their high cost and relatively low catalytic activity. The present invention provides the benefits of reduced costs, higher catalytic activity, and in some cases improved reaction selectivity. Other commercially important applications for PFIEP/silica catalysts of the present invention comprise hydrocarbon isomerizations and polymerizations; carbonylation and carboxylation reactions; hydrolysis and condensation reactions, esterifications and etherification; hydrations and oxidations; aromatic acylation, alkylation and nitration; and isomerization and metathesis reactions.

The present invention provides an improved process for the nitration of an aromatic compound wherein the improvement comprises contacting the aromatic compound with a microcomposite of the present invention as a catalyst. For example, in the nitration of benzene, a solution comprising benzene and optionally, a desiccant such as $MgSO_4$, is heated, typically to reflux at atmospheric pressure under an inert atmosphere, and a nitrating agent, for example, $HNO_3$ is added. The process is conducted under normal nitration conditions which conditions, such as temperature, are dependent upon the reactivity of the aromatic used. When a microcomposite of the present invention is used as a catalyst in the benzene solution, a high rate of conversion and selectivity to nitrobenzene is demonstrated as compared to "NAFION®" PFIEP alone or to the use of no catalyst (see Table I, Example 42). A preferred catalyst for this process is a microcomposite of the present invention wherein the perfluorinated ion-exchange polymer contains pendant sulfonic acid groups and wherein the metal oxide is silica, alumina, titania, germania, zirconia, alumino-silicate, zirconyl-silicate, chromic oxide and/or iron oxide. Most preferred is wherein the perfluorinated ion-exchange polymer is a "NAFION®" PFIEP and the metal oxide is silica, the most preferred "NAFION®" PFIEP having approximately 6.3 tetrafluoroethylene (TFE) molecules for every perfluoro(3,6-dioxa-4-methyl-7-octenesulfonyl fluoride) molecule ($CF_2$=CF—O—[$CF_2$CF($CF_3$)]—O—$CF_2CF_2$—$SO_2F$ (PSEPVE)) and an equivalent weight of approximately 1070.

The present invention further provides an improved process for the esterification of a carboxylic acid by reaction with an olefin wherein the improvement comprises contacting said carboxylic acid with a porous microcomposite of the present invention as a catalyst. For example, the esterification of acetic acid with cyclohexene to yield cyclohexylacetate. This esterification is typically carried out in a reactor. The acetic acid and cyclohexene solution typically comprises excess acetic acid to minimize dimerization of the cyclohexene. Generally, the reaction is run under normal esterification conditions which conditions are dependent upon the reactivity of the carboxylic acid and olefin used. Using as catalyst a microcomposite of the present invention results in specific activity almost an order of magnitude higher than that of other catalysts (see Table II, Example 43).

A preferred catalyst for this process is a microcomposite of the present invention wherein the perfluorinated ion-exchange polymer contains pendant sulfonic acid groups and wherein the metal oxide is silica, alumina, titania, germania, zirconia, alumino-silicate, zirconyl-silicate, chromic oxide and/or iron oxide. Most preferred is wherein the perfluorinated ion-exchange polymer is a "NAFION®" PFIEP and the metal oxide is silica, the most prefered "NAFION®" PFIEP having approximately 6.3 tetrafluoroethylene (TFE) molecules for every perfluoro perfluoro(3, 6-dioxa-4-methyl-7-octenesulfonyl fluoride) molecule ($CF_2=CF—O—[CF_2CF(CF_3)]—O—CF_2CF_2—SO_2F$ (PSEPVE)) and has an equivalent weight of approximately 1070.

The present invention also provides an improved process for the alkylation of an aromatic compound with an olefin wherein the improvement comprises using the microcomposite of the present invention as a catalyst. For example, in the alkylation of toluene with n-heptene, the toluene and heptene are dried before use and then mixed and heated, for example, to about 100° C. Dried catalyst comprising the porous microcomposite of the present invention is added to the toluene/n-heptene solution and left to react. This improved process is generally conducted under normal alkylation conditions which conditions are dependent upon the reactivity of the aromatic and olefin used. A high rate of conversion is found using a microcomposite of the present invention as compared to using "NAFION®" NR 50 PFIEP as the catalyst. The preferred catalyst for this process is a microcomposite of the present invention wherein the perfluorinated ion-exchange polymer contains pendant sulfonic acid groups and wherein the metal oxide is silica, alumina, titania, germania, zirconia, alumino-silicate, zirconyl-silicate, chromic oxide and/or iron oxide. Most preferred is wherein the perfluorinated ion-exchange polymer is a "NAFION®" PFIEP and the metal oxide is silica, the most preferred "NAFION®" PFIEP having approximately 6.3 tetrafluoroethylene (TFE) molecules for every perfluoro(3, 6-dioxa-4-methyl-7-octenesulfonyl fluoride) molecule ($CF_2=CF—O—[CF_2CF(CF_3)]—O—CF_2CF_2—SO_2F$ (PSEPVE)) and has an equivalent weight of approximately 1070.

The present invention also provides an improved process for the polymerization of tetrahydrofuran to polytetrahydrofuran. The product is polytetramethylene ether acetate (PTMEA), the diacetate of polytetrahydrofuran, which can be used in the preparation of "TERATHANE®" polyether glycol (E. I. du Pont de Nemours and Company, Wilmington, Del.). A process for the polymerization of tetrahydrofuran generally comprises contacting tetrahydrofuran with acetic anhydride and acetic acid in solution usually within a pressure reactor equipped with an agitator. The reaction can be conducted at ambient temperature. The improvement herein comprises adding to the solution as a catalyst the porous microcomposite of the present invention. Contact time can range from 1 hr to 24 hrs.

The present invention further provides an improved process for the acylation of an aromatic compound with an acyl halide to form an aryl ketone. A process for the acylation of an aromatic compound generally comprises heating the compound with the acyl halide. The improvement herein comprises contacting the aromatic compound with a catalytic porous microcomposite of the present invention. After allowing sufficient time for the reaction to complete, the aryl ketone product is recovered.

The present invention also provides an improved process for the dimerization of an alpha substituted styrene. The improvement comprises contacting the styrene with a catalytic porous microcomposite of the present invention. When using alpha methyl styrene, for example, the styrene may be heated in solution and the catalyst added. The product comprises a mixture of unsaturated dimers (2,4-diphenyl-4-methyl-1-pentene and 2,4-diphenyl-4-methyl-2-pentene) and saturated dimers (1,1,3-trimethyl-3-phenylidan and cis and trans-1,3-dimethyl-1,3-diphenylcyclobutane).

A preferred catalyst for the polymerization of tetrahydrofuran, for the acylation of an aromatic compound and for the dimerization of an alpha substituted styrene is a microcomposite of the present invention wherein the perfluorinated ion-exchange polymer contains sulfonic acid groups and wherein the metal oxide is silica, alumina titania, germania, zirconia, alumino-silicate, zirconyl-silicate, chromic oxide and/or iron oxide. Most preferred is wherein the PFIEP is a "NAFION®" PFIEP and the metal oxide is silica, the most preferred "NAFION®" PFIEP having approximately 6.3 tetrafluoroethylene (TFE) molecules for every perfluoro(3,6-dioxa-4-methyl-7-octenesulfonyl fluoride) molecule ($CF_2=CF—O—[CF_2CF(CF_3)]—O—CF_2CF_2—SO_2F$ (PSEPVE)) and has an equivalent weight of approximately 1070.

The microcomposite product of the present invention can be converted to a metal cation-exchanged material, as described by Waller (Catal. Rev. Sci. Eng. 28(1), 1–12 (1986)) for PFIEP resins. Such materials are also useful as catalysts.

Traditionally, olefin isomerization and alkylation with paraffins have been catalyzed by liquid mineral acids such as $H_2SO_4$, HF or $AlCl_3$. Environmental concerns associated with corrosive mineral acid catalysts have encouraged process changes and the development of solid-bed catalyst processes.

It is especially desirable to convert 1-butene to 2-butenes prior to use in the HF catalyzed alkylation process because the quality of the alkylates from 2-butenes (96–98 research octane number (RON) are significantly better than that from the 1-butene feed (87–89 RON). Extensive studies have been carried out on the solid acid catalyzed 1-butene isomerization to 2-butenes and to isobutene. 1-Butene isomerization to 2-butenes has been widely used as a model reaction of characterizing solid acid catalysts as well. It is clear that 1-butene isomerization to 2-butenes is not a very demanding reaction in terms of acid strength; several of solid acid are capable of catalyzing this isomerization involving the double bond shifting reaction. However, there remain important incentives for developing catalysts that can operate efficiently at lower temperatures. First, competing oligomerization reactions which not only result in yield losses, but also lead to catalyst deactivation generally become more significant at higher temperatures. Second, the equilibrium isomer distribution increasingly favors 2-butenes at lower temperatures.

Various solid acid catalysts and even amorphous silica-alumina are capable of catalyzing the 1-butene isomerization to 2-butenes at near ambient temperatures, but rapid deactivation is frequently encountered. Acidic cation exchange resin, sulfonic styrene-divinylbenzene copolymer ("AMBERLYST 15®") was shown to be active for the 1-butene isomerization to 2-butenes (see T. Uematsu, Bull. Chem. Soc. Japan, 1972, 45, 3329).

The present invention provides a process for the isomerization of an olefin comprising contacting said olefin at isomerization conditions with a catalytic amount of the microcomposite of the present invention.

Olefin isomerization processes can be directed towards either skeletal isomerization, double bond isomerization or geometric isomerization. Skeletal isomerization is concerned with reorientation of the backbone of the carbon structure, for example 1-butene to isobutene. Double bond isomerization is concerned with relocation of the double bond between carbon atoms while maintaining the backbone of the carbon struucture, for example 1-butene to 2-butene. Conversions between, for example cis and trans 2-pentenes, are known as geometric isomerization. The present invention provides primarily for double bond isomerization and includes some geometric isomerization. Skeletal isomerization is also provided to a limited degree at higher temperatures.

Preferred olefins are $C_4$ to $C_{40}$ hydrocarbons having at least one double bond, the double bond(s) being located at a terminal end, an internal position or at both a terminal and internal position. Most preferred olefins have 4 to 20 carbon atoms. The olefin can be straight-chained (normal) or branched and may be a primary or secondary olefin and thus substituted with one or more groups that do not interfere with the isomerization reaction. Such substituted groups that do not interfer with the isomerization reaction could include alkyl, aryl, halide, alkoxy, esters, ethers, or thioethers. Groups that may interfere with the process would be alcohols, carboxylic acids, amines, aldhehydes and ketones. The porous microcomposite used in the present process is described in detail above and comprises a perfluorinated ion-exchange polymer containing pendant sulfonic and/or carboxylic acid groups entrapped within and highly dispersed throughout a network of metal oxide, wherein the weight percentage of perfluorinated ion-exchange polymer in the microcomposite is from about 0.1 to 90 percent, preferably from about 5 to about 80 percent, most preferably from about 5 to about 20 percent and wherein the size of the pores in the microcomposite is about 0.5 nm to about 75 nm.

A preferred catalyst for the present olefin isomerization process is the microcomposite of the present invention wherein the perfluorinated ion-exchange polymer contains sulfonic acid groups and wherein the metal oxide is silica, alumina titania, germania, zirconia, alumino-silicate, zirconyl-silicate, chromic oxide and/or iron oxide. Most preferred is wherein the perfluorinated ion-exchange polymer is a "NAFION®" PFIEP and the metal oxide is silica, the most preferred "NAFION®" PFIEP having approximately 6.3 moles of tetrafluoroethylene (TFE) molecules per mole of perfluoro(3,6-dioxa-4-methyl-7-octenesulfonyl fluoride) molecule ($CF_2=CF-O-[CF_2CF(CF_3)]-O-CF_2CF_2-SO_2F$ (PSEPVE)) and an equivalent weight of approximately 1070.

In another embodiment, macroporosity (pore sizes about 75 to about 1000 nm) is also introduced into the microcomposite used in the present olefin isomerization process, resulting in the microcomposite having both increased surface area from the micropores and mesopores (0.5–75 nm) and enhanced accessibility resulting from the macropores (75–1000 nm).

Contacting of the olefin with the catalyst can be effected by using the catalyst in a fixed-bed system, a moving-bed system, a fluidized-bed system, or in a batch-type operation. Reactants can contact the catalyst in the liquid phase, a mixed vapor-liquid phase, or a vapor phase. The reactants can contact the catalyst in the absence of hydrogen or in the presence of hydrogen in a molar ratio of hydrogen to olefin of from about 0.01 to about 10. "Absence of hydrogen" means that free or molecular hydrogen is substantially absent in the combined reactant feed to the process.

Hydrogen, if present, can be supplied totally from outside the isomerization process, or the outside hydrogen may be supplemented by hydrogen separated from reaction products and recycled. Inert diluents such as helium, nitrogen, argon, methane, ethane and the like can be present either in association with hydrogen or in the absence of hydrogen. Although the principal isomerization reaction does not consume hydrogen, there can be net consumption of hydrogen in side reactions.

The isomerization of olefins is well known to be limited by the thermodynamic equilibrium of the reacting species. Isomerization conditions for the present process comprise reaction temperatures generally in the range of about 0° C. to about 300° C., preferably from about 25° C. to about 250° C. Pressure can range from ambient for gas phase or pressure sufficient to keep reaction in the liquid phase. Reactor operating pressures usually will range from about one atmosphere to about 100 atmospheres, preferably from about one atmosphere to about 50 atmospheres. The amount of catalyst in the reactor will provide an overall weight hourly space velocity (WHSV) of from about 0.1 to 100 $hr^{-1}$, preferably from about 0.1 to 10 $hr^{-1}$; most preferably 0.1 to 2 $hr^{-1}$.

Long contact time during olefin isomerization can create undesirable by-products, such as oligomers. The process of the present invention utilizes short contact times which cuts down on the amount of undesirable by-products. Contact times for the present process range from about 0.01 hr to about 10 hrs; preferably 0.1 hr to about 5 hrs. Contact time may be reduced at higher temperatures.

The particular product-recovery scheme employed is not deemed to be critical to the present invention; any recovery scheme known in the art may be used. Typically, the reactor effluent will be condensed and the hydrogen and inerts removed therefrom by flash separation. The condensed liquid product then is fractionated to remove light materials from the liquid product. The selected isomers may be separated from the liquid product by adsorption, fractionation, or extraction.

Olefin isomerization is useful in converting compounds into isomers more useful for particular applications. Olefins with the double bond at a terminal end tend to be more reactive and are easy to oxidize which can cause problems with their storage. Therefore, a shift to a more stable form can be desirable.

A high rate of conversion is found using the microcomposite of the present invention. Data in FIG. 1 shows that the microcomposite is very efficient for the 1-butene to 2-butenes isomerization reaction under mild conditions. Even at 50° C., near thermodynamic equilibrium values are obtained, which at 50° C. are 4.1%, 70.5% and 25.4% for 1-butene, trans-2-butene and cis-2-butene, respectively, and the experimental data are 6.6%, 66.9% and 26.5%, respectively at WHSV of 1-butene of 1 $hr^{-1}$. The effective activation energy for 1-butene isomerization to 2-butenes was determined to be 16.0 kcal/mol over the 13 wt % "NAFION®" PFIEP/silica microcomposite used (see Example 58). Comparisons performed in Example 57 show that "NAFION®" NR50 at 50° C. produced less than 1% conversion of the 1-butene, and at a temperature which could effectively catalyze the butene (200° C.) significant oligomers are also formed.

A study on the effect of temperature was carried out with a very diluted feed of 1-butene and at very low WHSV of 1-butene (see Table 4a, Example 58). Since near equilibrium n-butene distribution was obtained at 50° C., the main interest was on the isobutene formation. However, extremely small amounts, well below the equilibrium concentration, of isobutene was formed even at the highest temperature employed (250° C.). Due to the very low WHSV of 1-butene employed (Table 4a), the oligomers formed were quite pronounced. However, oligomers as well as isobutene formed over the microcomposite catalyst were less than that produced from the "NAFION®" NR50 beads catalyst under the same reaction conditions (see Table 2a, Example 57), and they are both in negligible amounts at low temperatures (<100° C.). Even though no pronounced catalyst deactivation was observed over more than 12 hr for the 1-butene isomerization to 2-butenes, the formation of isobutene and oligomers decreased rather rapidly at temperatures >100° C. The data listed in the Tables are obtained after about one hour on stream in all cases. These results suggest that isobutene could be formed through the cracking of butene oligomers which are favored at this temperature and low WHSV or 1-butene.

Overall, the extremely low surface area "NAFION®" NR50 beads result in low activity for the 1-butene isomerization under the reaction conditions employed. However, the intrinsic isomerization activity of the active sites in "NAFION®" is high and when present in a more accessible microstructure it becomes a very effective catalyst. Very high catalytic activity was observed for the 13 wt % "NAFION®" PFIEP/silica microcomposite material for which equilibrium distribution of n-butene can be readily obtained at 50° C. and is about 5–6 times more active than the "AMBERLYST 15®" catalyst.

The microcomposite product of the present invention is useful in a range of catalytic reactions as described above. For some of these reactions, some brown coloration may form upon the catalyst. Catalysts of the present invention can be regenerated by treatment with an acid, for example nitric acid. The microcomposite catalyst is contacted with the acid and then stirred at a temperature ranging from about 15° C. to about 100° C. for about 1 hr to about 26 hrs. Subsequent washing with de-ionized water is used to remove excess acid. The catalyst is then dried at a temperature ranging from about 100° C. to about 200° C., preferably under vacuum for about 1 hr to about 60 hrs to yield the regenerated catalyst.

EXAMPLES

"NAFION®" PFIEP solutions can be purchased from Aldrich Chemical Co., Milwaukee, Wis., or PFIEP solutions generally can be prepared using the procedure of U.S. Pat. No. 5,094,995 and U.S. Pat. No. 4,433,082. The "NAFION®" PEIEP solution referred to in the examples below is, unless otherwise noted, "NAFION®" NR 005, a "NAFION®" solution available from DuPont Nafion® Products, Fayetteville, NC., and also known as "NAFION®" SE-5110, and is prepared from resin which is approximately 6.3 (TFE) molecules for every perfluoro(3, 6-dioxa-4-methyl-7-octenesulfonyl fluoride) molecule $(CF_2=CF-O-[CF_2CF(CF_3)]-O-CF_2CF_2-SO_2F$ (PSEPVE)) and an equivalent weight of approximately 1070. "NAFION®" NR50 PFIEP, the same resin used to prepare the NR005 (SE-5110) solution is available in pellet form from E. I. du Pont de Nemours and Company, Wilmington, Del. (distributed by Aldrich Chemical Company). NAFION®" NR55 PFIEP is similarly available and structured with carboxylic ends as well as sulfonated ends on the pendant groups. "AMBERLYST 15®" sulfonated resin is a registered trademark of Rohm and Haas, Philadelphia, Pa. and is sold commercially by Rohm and Haas.

Example 1

Preparation of a 40 wt % "NAFION®"/60 wt % Silica Composite

To 200 mL of a "NAFION®" perfluorinated resin solution (which consists of 5 wt % "NAFION®" PFIEP in a mixture of lower alcohols and water) was added 25 g of a 0.4 M NaOH and the solution was stirred. Separately, in another beaker, to 34 g of tetramethoxy silane $[Si(OCH_3)_4]$ was added 5.44 g of distilled water and 0.5 g of 0.04 M HCl and the solution rapidly stirred for 10 minutes. After 10 minutes the silicon containing solution was added to the rapidly stirring "NAFION®" solution and stirring was continued for about 10 seconds to ensure good mixing. The solution was left to stand. It was observed that the whole solution formed a gel within a few seconds (typically 15 sec to 1 minute). The gel was covered and left to stand for 24 hours after which time the cover was removed and the gel was placed in an oven at 90° C. with a slow stream of nitrogen flushing through the oven. The gel was left to dry for 15 hours. The resultant dry glass-like pieces were then further dried at 140° C. under vacuum for 15 hours. The resultant material was re-acidified with HCl as follows, to convert the perfluorosulfonic acid into the acidic, active form. The dried material was placed in 100 mL of 3.5 M HCl and the mixture stirred for 1 hour. The HCl solution was removed via filtration and the solid resuspended in 100 mL of 3.5 M HCl and stirred for a further hour. The filtering and acidification step was repeated a total of five times. Finally, the solid was placed in distilled deionized water (200 mL) and stirred for 1 hour, filtered and resuspended in water (200 mL) and stirred in order to remove the excess HCl. The solid was filtered and dried at 140° C. for 24 hours. The yield was about 22 g. The final material was a finely particulate glass-like material with a light yellow coloration. The content of the "NAFION®" PFIEP was about 40 wt %. The solid had a hard texture typical of sol-gel derived silica type materials with some pieces up to a few mm in size. The material was highly porous with a surface area of 200 $m^2$ per gram (BET surface area), a single point pore volume of 0.38 cc/g and an average pore diameter of 5.59 nm.

Example 2

Preparation of a 40 wt % "NAFION®" PFIEP/60 wt % Silica Composite

To 200 mL of a "NAFION®" perfluorinated resin solution (which consists of 5 wt % "NAFION®" PFIEP in a mixture of lower alcohols and water) was added 25 g of a 0.4 M NaOH and the solution stirred. Separately, in another beaker, to 34 g of tetramethoxy silane $[Si(OCH_3)_4]$ was added 5.44 g of distilled water and 0.5 g of 0.04 M HCl and the solution rapidly stirred for 10 minutes. After 10 minutes the silicon containing solution was added to the rapidly stirring "NAFION®" solution and stirring was continued for about 10 seconds to ensure good mixing. The solution was left to stand; it was observed that the whole solution formed a gel within a few seconds (typically 15 sec to 1 minute). The gel was covered and left to stand in an oven at 75° C. for 8 hours at which time the cover was removed and the gel was placed in an oven at 90° C. with a slow stream of nitrogen flushing through the oven. The gel was left to dry for 15 hours. The resultant dry glass-like pieces were then further dried at 140° C. under vacuum for 15 hours. The resultant material was re-acidified with HCl as follows, to convert the perfluorosulfonic acid into the acidic, active form. The dried material was placed in 100 mL of 3.5 M HCl and the mixture stirred for 1 hour. The HCl solution was removed via filtration and the solid resuspended in 100 mL of 3.5 M HCl and stirred for a further hour. The filtering and acidification step was repeated a total of five times. Finally the solid was placed in distilled deionized water (200 mL) and stirred for 1 hour, filtered and resuspended in water (200 mL) and stirred in order to remove the excess HCl. The solid was filtered and dried at 140° C. for 24 hours. The yield was about 22 g. The final material was a glass like material with a light yellow coloration. The content of the "NAFION®" PFIEP was about 40 wt %. The solid had a hard texture typical of sol-gel derived silica type materials. The material was highly porous with a surface area of 131 $m^2$ per gram (BET surface area), a single point pore volume of 0.36 cc/g and an average pore diameter of 8.3 nm.

Example 3

Preparation of a 40 wt % "NAFION®" PFIEP/60 wt % Silica Composite

To 100 mL of a "NAFION®" perfluorinated resin solution (which consists of 5 wt % "NAFION®" PFIEP in a mixture of lower alcohols and water) was added 15 g of a 0.4 M NaOH and the solution stirred. 17 g of tetramethoxy silane was added to the rapidly stirring "NAFION®" solution and stirring was continued for about 10 seconds to ensure good mixing. The solution was left to stand; it was observed that the whole solution formed a gel within about a minute. The gel was covered and placed in an oven at 75° C. for 8 hours after which point the cover was removed and the gel was placed in an oven at 75° C. with a slow stream of nitrogen flushing through the oven. The gel was left to dry for 15 hours. The resultant dry glass-like pieces were then further dried at 140° C. under house vacuum for 15 hours. The resultant material was re-acidified with HCl as follows, to convert the perfluorosulfonic acid into the acidic, active form. The dried material was placed in 75 mL of 3.5 M HCl and the mixture stirred for 1 hour. The HCl solution was removed via filtration and the solid resuspended in 75 mL of 3.5 M HCl and stirred for a further hour. The filtering and acidification step was repeated a total of five times. Finally the solid was placed in distilled deionized water (100 mL) and stirred for 1 hour, filtered and resuspended in water (100 mL) and stirred in order to remove the excess HCl. The solid was filtered and dried at 140° C. for 24 hours. The yield was about 11 g. The final material was a glass-like material with a light yellow coloration. The content of the "NAFION®" PFIEP was 40 wt %. The solid had a hard texture typical of sol-gel derived silica type materials. The material is highly porous with a surface area of 134 $m^2$ per gram (BET surface area), a single point pore volume of 0.37 cc/g and an average pore diameter of 8.2 nm.

Example 4

Preparation of a 40 wt % "NAFION®" PFIEP/60 wt % Silica Composite

To 200 mL of a "NAFION®" perfluorinated resin solution (which consists of 5 wt % "NAFION®" PFIEP in a mixture of lower alcohols and water) was added 17 g of a 0.4 M NaOH and the solution stirred. Separately, in another beaker to 34 g of tetramethoxy silane [Si(OCH$_3$)$_4$] was added 5.44 g of distilled water and 0.5 g of 0.04 M HCl and the solution rapidly stirred for minutes. After 10 minutes the silicon containing solution was added to the rapidly stirring "NAFION®" solution and stirring was continued for about 10 seconds to ensure good mixing. The solution was left to stand; it was observed that the whole solution formed a gel within a few seconds (typically sec to 2 min). The gel was covered and left to stand for 24 hours after which point the cover was removed and the gel was placed in an oven at 90° C. with a slow stream of nitrogen flushing through the oven. The gel was left to dry for hours. The resultant dry glass-like pieces were then further dried at 140° C. under house vacuum for 15 hours. The resultant material was reacidified with HCl as follows, to convert the perfluorosulfonic acid into the acidic, active form. The dried material was placed in 100 mL of 3.5 M HCl and the mixture stirred for 1 hour. The HCl solution was removed via filtration and the solid resuspended in 100 mL of 3.5 M HCl and stirred for a further hour. The filtering and acidification step was repeated a total of five times. Finally the solid was placed in distilled deionized water (200 mL) and stirred for 1 hour, filtered and resuspended in water (200 mL) and stirred in order to remove the excess HCl. The solid was filtered and dried at 140° C. for 24 hours. The yield was about 22 g. The final material was a glass-like material with a light yellow coloration. The content of the "NAFION®" PFIEP was 40 wt %. The solid had a hard texture typical of sol-gel derived silica type materials with some pieces up to a few mm in size. The material was highly porous with a surface area of 294 $m^2$ per gram (BET surface area), a single point pore volume of 0.30 cc/g and an average pore diameter of 3.5 nm.

Example 5

Preparation of a ca. 20 wt % "NAFION®" PFIEP/ 80 wt % Silica Composite

To 100 mL of a "NAFION®" perfluorinated resin solution (which consists of 5 wt % "NAFION®" PFIEP in a mixture of lower alcohols and water) was added 25 g of a 0.4 M NaOH and the solution stirred. Separately, in another beaker to 34 g of tetramethoxy silane [Si(OCH$_3$)$_4$] was added 5.44 g of distilled water and 0.5 g of 0.04 M HCl and the solution rapidly stirred for 10 minutes. After 10 minutes the silicon containing solution was added to the rapidly stirring "NAFION®" solution and stirring was continued for about seconds to ensure good mixing. The solution was left to stand; it was observed that the whole solution formed a gel within a few seconds (typically 15 sec to 1 min). The gel was covered and left to stand for 24 hours after which point the cover was removed and the gel was placed in an oven at 90° C. with a slow stream of nitrogen flushing through the oven. The gel was left to dry for hours. The resultant dry glass-like pieces were then further dried at 140° C. under house vacuum for 15 hours. The resultant material was reacidified with HCl as follows, to convert the perfluorosulfonic acid into the acidic, active form. The dried material was placed in 100 mL of 3.5 M HCl and the mixture stirred for 1 hour. The HCl solution was removed via filtration and the solid resuspended in 100 mL of 3.5 M HCl and stirred for a further hour. The filtering and acidification step was repeated a total of five times. Finally the solid was placed in distilled deionized water (200 mL) and stirred for 1 hour, filtered and resuspended in water (200 mL) and stirred in order to remove the excess HCl. The solid was filtered and dried at 125° C. for 24 hours. The final material was a glass-like material with a light yellow coloration. The content of the "NAFION®" PFIEP was about 20 wt %. The solid had a hard texture typical of sol-gel derived silica type materials. The material was highly porous with a surface area of 287 $m^2$ per gram (BET surface area), a single point pore volume of 0.63 cc/g and an average pore diameter of 6.70 nm.

Example 6

Preparation of a ca. 10 wt % "NAFION®"/90 wt % Silica Composite

To 50 mL of a "NAFION®" perfluorinated resin solution (which consists of 5 wt % "NAFION®" PFIEP in a mixture of lower alcohols and water) was added 25 g of a 0.4 M NaOH and the solution stirred. Separately, in another beaker to 34 g of tetramethoxy silane [Si(OCH$_3$)$_4$] was added 5.44 g of distilled water and 0.5 g of 0.04 M HCl and the solution rapidly stirred for 10 minutes. After 10 minutes the silicon containing solution was added to the rapidly stirring "NAFION®" solution and stirring was continued for about 10 seconds to ensure good mixing. The solution was left to stand; it was observed that the whole solution formed a gel within a few seconds (typically 15 sec to 1 min). The gel was covered and left to stand for 24 hours after which point the cover was removed and the gel was placed in an oven at 90° C. with a slow stream of nitrogen flushing through the oven. The gel was left to dry for 15 hours. The resultant dry glass-like pieces were then further dried at 140° C. under house vacuum for 15 hours. The resultant material was reacidified with HCl as follows, to convert the perfluorosulfonic acid into the acidic, active form. The dried material was placed in 100 mL of 3.5 M HCl and the mixture stirred for 1 hour. The HCl solution was removed via filtration and the solid resuspended in 100 mL of 3.5 M HCl and stirred for a further hour. The filtering and acidification step was repeated a total of five times. Finally the solid was placed in distilled deionized water (200 mL) and stirred for 1 hour, filtered and resuspended in water (200 mL) and stirred in order to remove the excess HCl. The solid was filtered and dried at 125° C. for 24 hours. The final material was a glass like material with a light yellow coloration. The content of the "NAFION®" PFIEP was about 10 wt %. The solid had a hard texture typical of sol-gel derived silica type materials. The material was highly porous with a surface area of 270 m$^2$ per gram (BET surface area), a single point pore volume of 0.59 cc/g and an average pore diameter of 6.50 nm.

Example 7

Preparation of "NAFION®" PFIEP 40 wt % and Silica 60 wt % with Dual Porosity having Both Large (ca. 500 nm) and Small (ca. 2–15 nm) Pores To 100 mL of the "NAFION®" solution (which consists of 5 wt % "NAFION®" PFIEP in a mixture of lower alcohols and water) was added 15 g of a 0.4 M NaOH and the solution stirred, 4 g of calcium carbonate (Albafil Specialty Minerals, Adams, Mass. with a particle size of about 0.5 microns) was added to the basic "NAFION®" and calcium carbonate mixture which was ultrasonicated for 1 minute to 10 minutes using a sonic probe (Heat Systems Inc., Farmingdale, N.Y.). Separately, in another beaker to 17 g of tetramethoxy silane [Si(OCH$_3$)$_4$] was added 2.7 g of distilled water and 0.25 g of 0.04 M HCl and the solution rapidly stirred for 10 minutes. After 10 minutes the silicon containing solution was added to the rapidly stirring "NAFION®" solution and stirring was continued for about 10 seconds to ensure good mixing. The solution was left to stand; it was observed that the whole solution formed a gel within a few seconds (typically 10 sec to 1 min). The gel was covered and left to stand for 4 hours after which point the cover was removed and the gel was-placed in an oven at 90° C. with a slow stream of nitrogen flushing through the oven. The gel was left to dry for 15 hours. The resultant dry glass-like pieces were then further dried at 140° C. under house vacuum for 15 hours. The resultant material was reacidified with HCl as follows, to convert the perfluorosulfonic acid into the acidic, active form and also to dissolve out the calcium carbonate. The dried material was placed in 100 mL of 3.5 M HCl and the mixture stirred for 1 hour. Upon addition of the acid a large amount of gas was evolved (due to the reaction of the acid with HCl). The HCl solution was removed via filtration and the solid resuspended in 100 mL of 3.5 M HCl and stirred for a further hour. The filtering and acidification step was repeated a total of five times. Finally the solid was placed in distilled deionized water (200 mL) and stirred for 1 hour, filtered and resuspended in water (200 mL) and stirred in order to remove the excess HCl. The solid was filtered and dried at 125° C. for 24 hours. The final material was a glass-like material with a light yellow coloration. The microstructure of the derived material was investigated using scanning electron microscopy. The micrograph clearly shows very large pores about 0.5–1 micron in size. Also using energy dispersive x-ray analysis, no Ca could be detected showing that most of the calcium carbonate has been removed upon reacidification. The material was highly porous with a surface area of 310 m$^2$ per gram (BET surface area), and a single point pore volume of 0.46 cc/g.

Example 8

Catalytic Testing of "NAFION®" PFIEP/Silica Composites Using the Alkylation of Toluene with n-Heptene It is well known in the art that solid acid catalysts can catalyze a range of reactions, for example, alkylation reactions. We describe the use of the silica/"NAFION®" PFIEP composites to catalyze the allgation of toluene with n-heptene, and measure the conversion of heptene and toluene using gas chromatography.

As a comparison we, also tested the catalytic activity of the "NAFION®" PFIEP itself which is available in pellet form from E. I. du Pont de Nemours and Company, Wilmington, Del. 19898 (distributed by Aldrich Chemical Company) and is known as "NAFION®" NR 50 PFIEP.

A typical reaction is described as follows.

Both toluene and heptene were dried over 3 A molecular sieve before use (dried for 24-hours). In a round bottom flask was added 15.6 g of toluene and 8.4 g of n-heptene, and a "TEFLON®" coated magnetic stirrer added. A reflux condenser was attached to the flask and a slow stream of nitrogen passed over the top of the reflux condenser to minimize moisture. The flask and contents were heated to 100° C. A sample of 1 gram of the "NAFION®" PFIEP/silica catalyst (which is made up of 40 wt % "NAFION®" PFIEP and 60 wt % silica) as described in Example 1 was gently ground to break down the large pieces (to give a material about 0.1 to 1 mm in size) and the solid dried in vacuum at 140° C. for 24 hours. The dried material was added to the toluene/n-heptene mixture and the solution stirred and left to react for exactly 2 hours. After 2 hours a sample was removed and the conversion of heptene was measured using gas chromatography. In the GC analysis dodecane was used as a standard. The conversion of heptene was measured to be 90% to 95%, leaving only 10% to 5% of the heptene unreacted.

As a comparison experiment, the catalytic activity of 0.4 g of "NAFION®" NR 50 PFIEP was tested. 0.4 g represents the same weight of "NAFION®" PFIEP as tested above for the composite. The exact same procedure was used, drying the "NAFION®" NR 50 PFIEP at 140° C. for 24 hours and adding the "NAFION®" NR 50 PFIEP to the stirred solution of toluene (15.6 g) and heptene (8.4 g) at 100° C. After 2 hour reaction time the conversion was found to be about 3%, leaving 97% of the heptene unreacted.

Example 9

The procedure as described in Example 7 was carried out exactly except in this case a 20 wt % "NAFION®" PFIEP/

80 wt % silica composite was evaluated for catalytic activity, prepared as described in Example 4. Using 1 g of catalyst (and 15.6 g toluene and 8.4 heptene) lead to a conversion of heptene of 79%. As a comparison, using 0.2 g of NR 50 lead to a conversion of between 1–2%.

Example 10

The procedure as described in Example 7 was carried out exactly except in this case a 10 wt % "NAFION®" PFIEP/90 wt % silica composite was evaluated for catalytic activity, prepared as described in Example 5. Using 1 g of catalyst (and 15.6 g toluene and 8.4 heptene) lead to a conversion of heptene of 75%. As a comparison, using an equivalent weight of 0.1 g of NR 50 lead to a conversion of less than 1% leaving more than 99% of the heptene unreacted.

Example 11

Preparation of a 40 wt % "NAFION®" PFIEP/60 wt % Silica Composite Using Sodium Silicate as the Silica Source 150 mL of a 9% sodium silicate solution, which was made up by taking 45.6 mL of a sodium silicate solution (which contained 29.6% of silica) in $SiO_2$ and adding sufficient distilled water to bring the volume up to 150 mL. The measured pH was about 12.5. The solution was cooled to about 10° C. using an ice bath. The solution was stirred and an DOWEX® cation exchange resin was added until the pH reached 2.5, over about 2–3 minutes. This process generated polysilicic acid. The solution was separated from the resin by filtration. 35 mL of a 5% "NAFION®" PFIEP in alcohol/water mixture was added to the above solution with rapid stirring and the stirrer was stopped after about 1 min. The solution was covered and placed in an oven for 17 h at 90° C., after which point the whole system formed a solid gel. The cover was removed and the material was dried in an oven at 90° C. for 24 hours, and finally dried under vacuum at 140° C. for 17 h. This yielded hard, glass like pieces, which are typical of silica gel, with sizes in the range of about 0.1 to 5 mm. The dried glass was reacidified in 3.5 M HCl (ca. 100 mL of acid), and was stirred and filtered and the process repeated five times. Finally the material was washed by stirring with water (100 mL) and filtering and repeating the process 2 times. The reacidified material was dried at 140° C. for 17 h, which yielded a glass like, slightly brown, "NAFION®" PFIEP/silica composite.

Catalytic Testing

Both toluene and n-heptene were dried over 3 A molecular sieve before use (dried for 24 hours). In a round bottom flask was added 15.6 g of toluene and 8.4 g of n-heptene, and a "TEFLON®" coated magnetic stirrer added. A reflux condenser was attached to the flask and a slow stream of nitrogen passed over the top of the reflux condenser to minimize moisture. The flask and contents were heated to 100° C. A sample of 1 gram of the "NAFION®" PFIEP/silica catalyst (which was made up of 10 wt % "NAFION®" PFIEP and 90 wt % silica) as described above was gently ground to break down the large pieces (to give a material about 0.1 to 1 mm in size) and the solid dried in vacuum at 140° C. for 24 hours. The dried material was added to the toluene/n-heptene mixture and the solution stirred and left to react for exactly 2 hours at 100° C. After 2 hours a sample was removed and the conversion of n-heptene was measured using gas chromatography. In the GC analysis dodecane was used as a standard. The conversion of heptene was measured to be 36%.

Example 12

Preparation of a 20 wt % "NAFION®" PFIEP/80 wt % Alumina Composite 49.2 g of aluminum tri-secbutoxide [$Al(OC_4H_9)_3$] was added to 362 mL of distilled water at 75° C. and the mixture was left to stir for 15 min. To the stirred solution was added 1.36 g of a 69% concentrated nitric acid solution and the material was transfered to a sealed jar, and left in an oven at 90° C. for 24 h. A free flowing aluminum containing solution resulted. The formation of alumina gels that form porous transparent alumina has been described by B. E. Yoldas, in J. Mat. Sci 10 (1975) 1856 and B. E. Yoldas, Ceramics Bulletin, 54 (1975) 289. To 200 mL of the above solution was added 20 mL of a 5% "NAFION®" PFIEP containing alcohol/water resin solution. The material was stirred on a hot plate with a solution temperature of 80° C. until all of the solvent evaporated, leaving a glass-like solid. The glass-like solid had particles in the range of about 0.1 to 2 mm. The material contained about 20 wt % "NAFION®" PFIEP and 80 wt % alumina. The material was reacidified with 4M HCl in dioxane.

Example 13

13.5 wt. % "NAFION®" PFIEP in Silica, with Pore Diameter ca. 10 nm 204 g of tetramethoxysilane (TMOS), 33 g of distilled water and 3 g of 0.04M HCl was stirred for 45 mins. to give a clear solution. To 300 mL of a "NAFION®" solution (which contains 5% of "NAFION®" PFIEP by weight) was added 150 mL of a 0.4M NaOH solution, while the "NAFION®" solution was being stirred. After addition of the sodium hydroxide solution the resulting solution was stirred for a further 15 min. The silicon containing solution, prepared as described above, was added rapidly to the stirred "NAFION®" containing solution. After about 10–15 seconds the solution gelled to a solid mass. The gel was placed in an oven and dried at a temperature of about 95° C., over a period of about 2 days, followed by drying under vacuum overnight. The hard glass-like product was ground and passed through a 10-mesh screen. The material was then stirred with 3.5M HCl for 1 hour (with 500 mL of acid), followed by washing with 500 mL of deionized water. The solid was collected by filtration. Acidification, washing and filtration were repeated a total of 5 times and after the final wash the solid was dried under vacuum at 100° C. for 24 hours. Yield of dried product was 98 g. The surface area (determined by BET), pore volume and pore diameter was determined to be 344 $m^2/g$, 0.85 cc/g and 9.8 nm, respectively.

Example 14

40 wt. % "NAFION®" PFIEP in Silica, with Pore Diameter ca. 10 nm 204 g of tetramethoxysilane (TMOS), 33 g of distilled water and 3 g of 0.04M HCl was stirred for 45 mins. to give a clear solution. To 1200 mL of a "NAFION®" solution (which contains 5% of "NAFION®" PFIEP by weight) was added 150 ml of a 0.4M NaOH solution, while the "NAFION®" solution was being stirred. After addition of the sodium hydroxide solution, the resulting solution was stirred for a further 15 min. The silicon containing solution, prepared as described above, was added rapidly to the stirred "NAFION®" containing solution. After about 10–15 seconds the solution gelled to a solid mass. The gel was placed in an oven and dried at a temperature of about 95° C., over a period of about 2 days, followed by drying under vacuum overnight. The hard glass-like product was ground and passed through a 10-mesh screen. The material was then stirred with 3.5M HCl for 1 hour (with 500 mL of acid) followed by washing with 500 mL of deionized water. The solid was collected by filtration. Acidification, washing and filtration were repeated a total of 5 times and after the final wash the solid was dried under vacuum at 100° C. for 24 h. Yield of dried product was 130 g. The surface area (determined by BET), pore volume and pore diameter was determined to be 468 m$^2$/g, 1.05 cc/g and 8.9 nm, respectively.

Example 15

8 wt. % "NAFION®" PFIEP in Silica, with Pore Diameter ca. 10 nm 204 g of tetramethoxysilane (TMOS), 33 g of distilled water and 3 g of 0.04M HCl was stirred for 45 mins. to give a clear solution. To 150 mL of a "NAFION®" solution (which contains 5% of "NAFION®" PFIEP by weight) was added 150 mL of a 0.4M NaOH solution, while the "NAFION®" solution was being stirred. The sodium hydroxide was added over about 1 min. After addition of the sodium hydroxide solution, the resulting solution was stirred for a further 15 min. The silicon containing solution, prepared as described above, was added rapidly to the stirred "NAFION®" containing solution. After about 10–15 seconds the solution gelled to a solid mass. The gel was placed in an oven and dried at a temperature of about 95° C., over a period of about 2 days, followed by drying under vacuum overnight. The hard glass-like product was ground and passed through a 10-mesh screen. The material was then stirred with 3.5M HCl for 1 hour (with 500 mL of acid), followed by washing with 500 mL of deionized water. The solid was collected by filtration. Acidification, washing and filtration were repeated a total of 5 times and after the final wash the solid was dried under vacuum at 100° C. for 24 h. Yield of dried product was 82 g. The surface area (determined by BET), pore volume and pore diameter was determined to be 412 m$^2$/g, 0.84 cc/g and 10.3 nm, respectively.

Example 16

13 wt. % "NAFION®" PFIEP in Silica, with Pore Diameter ca. 20 nm 204 g of tetramethoxysilane (TMOS), 33 g of distilled water and 3 g of 0.04M HCl was stirred for 45 mins. to give a clear solution. To 300 mL of a "NAFION® " solution (which contains 5% of "NAFION® " PFIEP by weight) was added 150 mL of a 0.8M NaOH solution, while the "NAFION®" solution was being stirred. After addition of the sodium hydroxide solution the resulting solution was stirred for a further 15 min. Both the silicon containing solution and the "NAFION®" containing solution were cooled in ice to lower the solution temperature to about 10° C. The silicon containing solution, prepared as described above, was added rapidly to the stirred "NAFION®" containing solution. After about 10 seconds the solution gelled to a solid mass. The gel was placed in an oven and dried at a temperature of about 90° C., over a period of about 2 days, followed by drying under vacuum overnight. The hard glass-like product was ground and passed through a 10-mesh screen. The material was then stirred with 3.5M HCl for 1 hour (with 500 mL of acid) followed by washing with 500 mL of deionized water. The solid was collected by filtration. Acidification, washing and filtration were repeated a total of 5 times and after the final wash the solid was dried under vacuum at 100° C. for 24 h. Yield of dried product was 97 g. The surface area (determined by BET), pore volume and pore diameter was determined to be 123 m$^2$/g, 0.84 cc/g and 22 nm, respectively.

Example 17

40 wt. % "NAFION@" PFIEP in Silica, with Both Small ca. 10 nm and Large ca. 0.5 µm Sized Pores, Dual Porosity Gels 255 g of tetramethoxysilane (TMOS), 40.75 g of distilled water and 3.75 g of 0.04M HCl was stirred for 45 mins. to give a clear solution. To 1500 mL of a "NAFION®" solution (which contains 5% of "NAFION®" PFIEP by weight) was added 187 mL of a 0.4M NaOH solution, while the Nafion solution was being stirred, followed by 187 g of calcium carbonate (supplied by Albafil Specialty Minerals). After addition of the sodium hydroxide solution, the resulting solution was sonicated for a further 15 min. using a Branson ultrasonic probe to ensure dispersion of the calcium carbonate. The silicon containing solution, prepared as described above, was added rapidly to the stirred "NAFION®" containing solution. After about 10–15 seconds the solution gelled to a solid mass. The gel was placed in an oven and dried at a temperature of about 95° C., over a period of about 2 days, followed by drying under vacuum overnight. The hard glass-like product was ground and passed through a 10-mesh screen. The material was then stirred with 3.5M HCl for 1 hour (with 500 mL of acid), followed by washing with 500 mL of deionized water. The solid was collected by filtration. Acidification, washing, and filtration were repeated a total of 5 times and after the final wash the solid was dried under vacuum at 100° C. for 24 h. Yield of dried product was 168 g. The surface area (determined by BET), pore volume and pore diameter was determined to be 57 m$^2$/g, 0.21 cc/g and 13 nm, respectively.

Example 18

13 wt. % "NAFION®" PFIEP in Silica, with Pore Diameter ca. 2.1 nm 204 g of tetramethoxysilane (TMOS), 33 g of distilled water and 3 g of 0.04M HCl was stirred for 30 mins. to give a clear solution. To 300 mL of a "NAFION®" solution, HCl was added to yield an HCl concentration of 0.01M. The silicon containing solution, prepared as described above, was added rapidly to the stirred "NAFION®" containing solution. The vessel was sealed and placed in a heated oven overnight at 65° C., after which point the system gelled. The top was removed and the flask and contents were placed in an oven and dried at a temperature of about 95° C., over a period of about 2 days, followed by drying under vacuum overnight. The hard glass-like product was ground and passed through a 10-mesh screen. The material was then stirred with 3.5M HCl for 1 hour (with 500 mL of acid), followed by washing with 500 mL of deionized water. The solid was collected by filtration. Acidification, washing and filtration were repeated a total of 5 times and after the final wash the solid was dried under vacuum at 100° C. for 24 h. Yield of dried product was 96 g. The surface area (determined by BET), pore volume and pore diameter was determined to be 563 m$^2$/g, 0.15 cc/g and 2.1 nm, respectively.

Example 19

42 wt. % "NAFION@" PFIEP in Silica, no Acid Hydrolysis step via TMOS

15 g of 0.4M NaOH was added to 100 mL of a 5% "NAFION®" solution. To this solution was added 17 g of TMOS and the solution gelled within 15 secs. The solid gel was dried at 95° C. in an oven vented with flowing nitrogen, for 2 days, followed by vacuum drying at 140° C. The solid was re-acidified with 3.5M HCl for 1 hour (with 50 mL of acid), followed by washing with 50 mL of de-ionized water. The solid was collected by filtration. Acidification, washing and filtration were repeated a total of 5 times and after the final wash the solid was dried under vacuum at 100° C. for 24 h. Yield of dried product was 9 g. The surface area (determined by BET), pore volume and pore diameter was determined to be 330 $m^2/g$, 0.36 cc/g and 8.3 nm, respectively.

Example 20

8 wt. % "NAFION®" in Silica, Adding Silica to "NAFION®", then the NaOH

20.4 g of TMOS, 3.2 g of water and 0.2 g of 0.04M HCl was stirred for 30 min. and added to 15 mL of 5% "NAFION®" solution with rapid stirring. To the silica and "NAFION®" containing solution, 15 g of 0.4M NaOH was rapidly added while the solution was rapidly stirred. The solution turned to a solid gel within about 10 seconds. The gel was dried at 98° C. for 2 days followed by drying under vacuum overnight at 100° C. The solid was re-acidified with 3.5M HCl for 1 hour (with 150 mL of acid), followed by washing with 50 mL of de-ionized water. The solid was collected by filtration. Acidification, washing and filtration were repeated a total of 5 times and after the final wash the solid was dried under vacuum at 100° C. for 24 h. Yield of dried product was 9 g. The surface area (determined by BET), pore volume and pore diameter was determined to be 364 $m^2/g$, 1.06 cc/g and 11.5 nm, respectively.

Example 21

"NAFION®" PFIEP/Silica Composite via Tetraethoxysilane

108 g of tetraethoxysilane, 28.8 g of water and 2.4 g of 0.04M HCl was stirred for 2.5 hours to give a clear solution. 55 mL of 0.4M NaOH was added to 75 mL of stirred "NAFION®" solution (5%) and the stirring continued for 15 mins. The silica solution was rapidly added to the stirring "NAFION®" solution and the system formed a gel within 10–15 seconds. The gel was dried at 95° C. for two days followed by vacuum drying at 125° C. overnight. The gel was ground and passed through a 10-mesh screen and re-acidified with 3.5M HCl for 1 hour (with 250 mL of acid), followed by washing with 250 mL of de-ionized water. The solid was collected by filtration. Acidification, washing and filtration were repeated a total of 5 times and after the final wash the solid was dried under vacuum at 100° C. for 24 h. Yield of dried product was 32 g. The surface area (determined by BET), pore volume and pore diameter was determined to be 330 $m^2/g$, 0.75 cc/g and 7.5 nm, respectively.

Example 22

"NAFION®" PFIEP/Silica Composite via Sodium Silicate Solution

To 100 g of sodium silicate solution (which contained 29% by weight of silica), was added 210 mL of water. To this solution 300 g of DOWEX® cation exchange resin was very quickly added and stirred rapidly until the pH dropped to about 3 (in less than 2 minutes). The solution was filtered. 30 mL of a 5% "NAFION®" solution was added to 150 mL of the filtrate while it was stirred. 5 mL of 2M NaOH was then added and the solution gelled; pH was close to 6.0. The gel was dried at 95° C. for two days and then dried under vacuum at 100° C. for 1 day. The gel was ground and passed through a 10-mesh screen and re-acidified with 3.5M HCl for 1 hour (with 250 mL of acid), followed by washing with 250 mL of de-ionized water. The solid was collected by filtration. Acidification, washing and filtration were repeated a total of 5 times and after the final wash the solid was dried under vacuum at 100° C. for 24 h. Yield of dried product was 15.6 g. The surface area (determined by BET), pore volume and pore diameter was determined to be 350 $m^2/g$, 0.74 cc/g and 7.1 nm, respectively.

Example 23

6 wt. % "NAFION®" PFIEP in Silica, Using Sodium Silicate Solution

50 g of distilled water was added to 20 g of a sodium silicate solution (which contained 29% by weight of silica). 10 g of a 5% "NAFION®" solution was added with rapid stirring. The solution was added dropwise over about 10 mins. Next, 24 mL of a 12.41% HCl solution was added while rapidly stirring, and the pH dropped to 1.8. Next, 0.4M NaOH was added rapidly to adjust the pH to 6, after which point the solution formed a gel. The gel was ground and passed through a 10-mesh screen and re-acidified with 3.5M HCl for 1 hour (with 100 mL of acid), followed by washing with 100 mL of de-ionized water. The solid was collected by filtration. Acidification, washing and filtration were repeated a total of 5 times and after the final wash the solid was dried under vacuum at 100° C. for 24 h. Yield of dried product was 6.5 g. The surface area (determined by BET), pore volume and pore diameter was determined to be 387 $m^2/g$, 0.81 cc/g and 7.1 nm, respectively.

Example 24

10 wt. % "NAFION®" PFIEP in Silica via "LUDOX®" 40 Colloidal Silica

200 mL of "LUDOX®" 40 (which contains 80 g of silica) was added to 160 mL of 5% "NAFION®" solution. The pH was adjusted to 6.0 using 3.5M HCl. The solution was placed in a sealed glass vessel and placed in an oven at 60–70° C. After 1 hour the system gelled. The material was dried at 90° C., followed by vacuum drying at 140° C. The gel was reacidified with 3.5M HCl for 1 hour (with 500 mL of acid), followed by washing with 500 mL of de-ionized water. The solid was collected by filtration. Acidification, washing and filtration were repeated a total of 5 times and after the final wash the solid was dried under vacuum at 100° C. for 24 h.

Example 25

A Composite of "NAFION®" (NR55) PFIEP in Silica

150 mL of a 5% solution of "NAFION®" (NR55, which contains both sulfonic acid and carboxylic acid groups), was added to 60 mL of isopropanol, 15 mL of methanol, and 75 mL of water. To this was added 150 g of 0.4M NaOH. Separately, 204 g of TMOS, 32.6 g of water and 3 g of 0.04M HCl was stirred for 20 mins and then added to the NR55 solution. The gel that formed was dried at 100° C. over 24 hrs, ground and passed through a 10-mesh screen. The material was then stirred with 3.5M HCl for 1 hour (with 500 mL of acid), followed by washing with 500 ml of de-ionized water. The solid was collected by filtration. Acidification, washing and filtration were repeated a total of 5 times and after the final wash the solid was dried under vacuum at 100° C. for 24 h. Yield of dried product was 92.6 g. The "NAFION®" PFIEP content was 7.5 wt %.

Example 26

"NAFION®" PFIEP Entrapped in Si—Al—Zr Composite 20.4 g of TMOS, 3.6 g of water and 0.3 g of 0.04M HCl was stirred for 20 mins. and added to 5 g of the mixed aluminum/zirconium complex ($Al_2Zr(OR)_x$ available from Gelest, Tullytown, Pa. The mixture was stirred for 5 mins. 30 g of 5% "NAFION®" solution and 15 g of 0.4M NaOH were mixed and added to the Si—Al—Zr containing solution, and the material was placed in an oven at 75° C. and dried at 100° C.

Example 27

Nitric Acid Treatment of Used or Organic Contaminated Composites

The above described materials of the present invention are used for a range of catalytic reactions. For some reactions, some brown coloration may form upon the catalyst. Catalysts can be regenerated by treatment with acid. 100 g of 13 wt. % "NAFION®" PFIEP in silica was mixed with 1 liter of 35% nitric acid and the solid stirred at 75° C. overnight. The white solid obtained was washed with de-ionized water to remove excess acid and was dried at 100° C. under vacuum overnight.

Example 28

Catalytic Testing of "NAFION®" PFIEP/Silica Composites Using the Alkylation of Toluene with n-Heptene It is well known in the art that solid acid catalysts can catalyze a range of reactions, for example, alkylation reactions. The silica/"NAFION®" PFIEP composites of the present invention can be used to catalyze the alkylation of toluene with n-heptene, measuring the conversion of n-heptene using gas chromatography.

As a comparison, the catalytic activity of "NAFION®" PFIEP itself which is available in pellet form from E. I. du Pont de Nemours and Company, Wilmington, Del., and is known as "NAFION®" NR 50, was also tested.

ILLUSTRATIVE EXAMPLE OF PRESENT INVENTION

Both toluene and n-heptene were dried over 3 A molecular sieve before use (dried for 24 hours). In a round bottom flask was added 15.6 g of toluene and 8.4 g of n-heptene, and a Teflon coated magnetic stirrer added. A reflux condenser was attached to the flask and a slow stream of nitrogen passed over the top of the reflux condenser to minimize moisture. The flask and contents were heated to 100° C. A sample of 1 g of the "NAFION®" PFIEP/silica catalyst as described in Example 14 was dried in vacuum at 150° C. for 15 hours. The dried material was added to the toluene/n-heptene mixture and the solution stirred and left to react for exactly 2 hours. After two hours a sample was removed and the conversion of n-heptene was measured using gas chromatography. In the GC analysis dodecane was used as a standard. The conversion of n-heptene was measured to be 98%, leaving only 2% of the heptene unreacted.

Comparative Example

As a comparison experiment, the catalytic activity of 0.4 g of "NAFION®" NR50 PFIEP was tested. 0.4 g represents the same weight of "NAFION®" PFIEP as tested above for the composite of the present invention. The exact same procedure was used, drying the NR50 at 150° C. for 24 hours and adding the NR50 to the stirred solution of toluene (15.6 g) and heptene (8.4 g) at 100° C. After 2 hour reaction time the conversion was found to be about 3%, leaving 97% of the heptene unreacted.

Example 29

The illustrative example as described in Example 28 was carried out with the exception that 1 g of the material from Example 13 was used in the catalysis run. Thus, 1 g of a 13 wt. % Nafion in silica was used. The conversion was found to be 89% of heptene.

As a comparative example, 0.13 g of "NAFION®" NR50 was used as catalyst (again with the same conditions as described in Example 28, comparative example). The measured conversion was about 1% of heptene.

Example 30

The illustrative example as described in Example 28 was carried out with the exception that 1 g of the material from Example 15 was used in the catalysis run. The conversion was found to be 84% of heptene.

Example 31

The illustrative example as described in Example 28 was carried out with the exception that 1 g of the material from Example 16 was used in the catalysis run. The conversion was found to be 94% of heptene.

Example 32

The illustrative example as described in Example 28 was carried out with the exception that 1 g of the material from Example 17 was used in the catalysis run. The conversion was found to be 97% of heptene.

Example 33

The illustrative example as described in Example 28 was carried out with the exception that 1 g of the material from Example 18 was used in the catalysis run. The conversion was found to be 91% of heptene.

Example 34

The illustrative example as described in Example 28 was carried out with the exception that 1 g of the material from Example 19 was used in the catalysis run. The conversion was found to be 83% of heptene.

Example 35

The illustrative example as described in Example 28 was carried out with the exception that 1 g of the material from Example 20 was used in the catalysis run. The conversion was found to be 93% of heptene.

Example 36

The illustrative example as described in Example 28 was carried out with the exception that 1 g of the material from Example 21 was used in the catalysis run. The conversion was found to be 86% of heptene.

Example 37

The illustrative example as described in Example 28 was carried out with the exception that 1 g of the material from Example 22 was used in the catalysis run. The conversion was found to be 82% of heptene.

Example 38

The illustrative example as described in Example 28 was carried out with the exception that 1 g of the material from Example 23 was used in the catalysis run. The conversion was found to be 76% of heptene.

Example 39

The illustrative example as described in Example 28 was carried out with the exception that 1 g of the material from Example 24 was used in the catalysis run. The conversion was found at to be 28% of heptene.

Example 40

The illustrative example as described in Example 28 was carried out with the exception that 1 g of the material from Example 25 was used in the catalysis run. The conversion was found to be 64% of heptene.

Example 41

Catalytic Testing of "NAFION®" PFIEP/silica composite Using the Dimerization of Alpha Methylstyrene (AMS)

The dimerization of alpha-methylstyrene (AMS) with "NAFION®" PFIEP has been studied in detail in the past (B. Chaudhuri and M. M. Sharme, Ind. Eng. Chem. Res. 1989, 28, 1757–1763). The products of the reaction are a mixture of the individual unsaturated dimers (2,4-diphenyl-4-methyl-1-pentene and 2,4-diphenyl-4-methyl-2-pentene) and the saturated dimers (1,1,3-trimethyl-3-phenylidan and cis and trans-1,3-dimethyl-1,3-diphenylcyclobutane). With "NAFION®" PFIEP as the catalyst, the reaction was found to be very slow.

ILLUSTRATIVE EXAMPLE OF THE PRESENT INVENTION 0.5 g of the solid made via Example 13 was used as catalyst. 5 g of alphamethylstyrene and 45 g of cumene as solvent was heated to 60° C. To this solution 0.5 g of the catalyst was added, and reagents and catalyst were stirred and heated at 60° C. After 30 mins. the amount of alphamethylstyrene was measured using GC analysis, which showed a conversion of about 99%, with less than 1% of the reactant AMS remaining. After 200 mins. of reaction time the conversion of AMS was about 100%.

Comparative Example 0.07 g of 100% "NAFION®" NR50 PFIEP was used as catalyst. 5 g of alphamethylstyrene and 45 g of cumene as solvent were heated to 60° C. To this solution 0.07 g of the catalyst was added, and reagents and catalyst were stirred and heated at 60° C. After 30 mins. the amount of alphamethylstyrene was measured using GC analysis, which showed a conversion of less than 1%, with more than 99% of the reactant AMS remaining. After 200 mins. of reaction time the conversion of alphamethylstyrene was about 5%, with 95% of the AMS unchanged.

Example 42

Catalytic Testing of "NAFION®" PFIEP/Silica Composite Using the Nitration of Benzene to Form Nitrobenzene A 250 mL three necked flask was equipped with a Dean-Stark moisture trap and a magnetic stirrer. The flask was loaded with 70–75 g benzene, 10 g $MgSO_4$ (as a desiccant), 5.0 g 1,3,5-trichlorobenzene (internal standard) and 7.5 g of the appropriate acid catalyst. The mixture was heated to reflux at atmospheric pressure, under inert atmosphere. After about 30 min. at reflux, a feed pump was turned on, and 90% $HNO_3$ was fed into the reactor at a rate of about 0.06 mL/min. The reaction mixture was maintained at reflux, and samples were removed at 15–30 minute intervals for GC analysis. The average nitric acid conversions and nitrobenzene selectivities, over the 150 min. run time are given below in Table I:

TABLE I

| Acid Catalyst | % $HNO_3$ Conversion | % Selectivity (nitrobenzene) |
|---|---|---|
| 13.5% "NAFION ®"/silica composite (from Example 13) | 82 ± 8 | 99.6 ± 0.2 |
| "NAFION ®" NR50 beads | 64 ± 8 | 98.8 ± 1.0 |
| None | 35 ± 7 | 97.9 ± 0.6 |

Example 43

Catalytic Testing of "NAFION®" PFIEP/Silica Composite Using the Conversion of Cyclohexene with Acetic acid to Cyclohexyl Acetate The esterification of cyclohexene with acetic acid using solid acid catalyst was carried out in liquid phase in a Fisher-Porter reactor. The reactor comprised of a glass tube fitted with a gas injection port, liquid sampling port, thermocouple, and pressure gauge. Mixing in the reactor was provided by a magnetic stirrer and the reactor was heated with a hot air gun. The glass reactor was operated in the batch mode with acetic acid, cyclohexene, cyclooctane (internal standard), and the catalyst loaded into the reactor before the reactor was pressurized and heated to the desired operating condition. The reactants and products were analyzed by gas chromatograph-mass spectrometer.

The reaction was performed in excess of acetic acid (acetic acid/cyclohexene molar ratio of 5:1) to minimize the dimerization of cyclohexene. Four different catalysts were tested at a temperature and pressure of 100° C. and 50 psig, respectively, for 5 hours time on stream. A blank run was also carried out under identical operating conditions to determine whether the reaction proceeds in the absence of any catalyst. Little or no cyclohexyl acetate was formed in the absence of catalyst under the operating conditions mentioned above.

The four catalysts tested in this series of experiments included sulfated zirconia, Amberlyst 15 (Rohm and Haas), "NAFION®" NR50 (DuPont), and 13.5% "NAFION®"

PFIEP/silica microcomposite material of the present invention (Example 13). The efficiency of the catalysts after 5 hours time on stream were compared on the basis of specific activity of the catalysts (measured as gmol of cyclohexyl acetate/g-cat.hr) for the esterification reaction. The specific activity of the catalysts have been reported in Table II.

TABLE II

| Catalyst | Specific Activity × $10^2$ (gmol cyclohexyl acetate) (gm catalyst) · (hr) |
|---|---|
| Sulfated Zirconia | 16.8 |
| Amberlyst 15 | 82.4 |
| "NAFION ®" NR50 | 86.3 |
| 13.5% "NAFION ®" PFIEP/silica | 677.5 |

Thus, the activity of 13.5 wt. % "NAFION®" PFIEP/silica microcomposite catalyst was found to be almost an order of magnitude higher than that of Amberlyst 15 and "NAFION®" NR50 and approximately 40 times higher than that of sulfated zirconia. The selectivity of cyclohexyl acetate was greater than 90 mole % for Amberlyst 15, "NAFION®" NR50, and 13.5 wt. % "NAFION®" PFIEP/silica microcomposite catalysts while the selectivity was less than 50 mole % for sulfated zirconia.

Example 44

Formation of "TERATHANE®" Using the "NAFION®" PFIEP/Silica Catalyst

A 300 mL "TEFLON®" lined Parr pressure reactor equipped with a mechanical agitator, an internal 420 micron filter, and a feed pump was loaded with 9 g "NAFION®" PFIEP/silica catalyst of Example 18 and filled the rest of the way with a solution comprising 27.9 parts 3-methyl tetrahydrofuran, 71.1 parts tetrahydrofuran, 6 parts acetic anhydride and 0.6 parts acetic acid. The reactor was assembled, air bled, and feeds started such that the average contact time in the reactor was 10 hrs. The reaction was conducted at ambient temperature. Polymer was produced at 5.9% conversion at 4000 Mn. More catalyst (34 g) was added for a total of 43 g, and the reaction continued. Polymer was produced at 20% conversion and 3500 Mn.

No analysis of 3-methyl THF content of polymer was done. This system of reactants with 9 g "NAFION®" NR50, 10 hr contact time would produce 45–50% conversions.

Example 45

80% "NAFION®" PFIEP/20% Silica Composite 40 g of TMOS, 7 g of water and 0.6 g of 0.04M HCl was stirred for 15 mins. This was added to 1200 mL of a 5% "NAFION®" solution (which had previously had 100 mL of 0.4M NaOH added over 5 mins. with stirring). A soft gel was formed and the flask and contents were placed in an oven at 95° C. under a nitrogen flow to dry. The hard glass-like product was ground and passed through a 10-mesh screen, and then the material was stirred with 3.5M HCl for 1 h (with 500 mL of acid), followed by washing with 500 mL of de-ionized water. The solid was collected by filtration. Acidification, washing and filtration were repeated a total of 5 times, and after the final wash the solid was dried under vacuum at 100° C. for 24 h. Yield of dried product was 58 g.

Example 46

Organically Modified Silica/"NAFION®" PFIEP Composite $SiO_2/SiO_{3/2}Me$/"NAFION®" PFIEP 20 g of $MeSi(OMe)_3$ was mixed with 3 g of water and 0.3 g of 0.04M HCl. The solution was stirred for about 5 mins. A solution of 22 g of TMOS, 3 g water and 0.3 g of 0.04M HCl (which was stirred for 3 mins.) was added to the MeSi-containing solution. The combined clear silicon containing solution was added to "NAFION®"/NaOH (60 mL of a 5% "NAFION®" solution which contains 30 mL of 0.4M NaOH added over 1 min.) and the system gelled in about 3–5 mins. The material was dried at 95° C. under a nitrogen flow. The hard glass-like product was ground and passed through a 10-mesh screen, and then the material was stirred with 3.5M HCl for 1 hour (with 100 mL of acid), followed by washing with 100 mL of de-ionized water. The solid was collected by filtration. Acidification, washing and filtration were repeated a total of 5 times, and after the final wash the solid was dried under vacuum at 100° C. for 24 h. Yield of dried product was about 20 g. The illustrative example as described in Example 28 was carried out with the exception that 1 g of the material from this example was used in the catalysis run. The conversion was found to be 44% of heptene.

Example 47

$PhSiO_{3/2}/MeSiO_{3/2}/Me_2SiO/SiO_2$/"NAFION®" PFIEP Composite 5 g of $PhSi(OMe)_3$, 10 g $MeSi(OMe)_3$, 10 g $Me_2Si(OMe)_2$ were mixed and 4 g of water and 0.3 g of 0.04M HCl was added and stirred. To this 22 g of TMOS which was stirred with 0.3 g of 0.04M HCl and 3 g of water was added and the silicon containing solution was stirred for 15 mins. To 40 g of the 5% "NAFION®" solution was added 25 ml of 0.4M NaOH over 1 min. Next the silicon containing solution was added to the stirred "NAFION®" solution and the mixture was left to gel. The material was dried at 95° C. under a nitrogen flow. The hard glass-like product was ground and passed through a 10-mesh screen, and then the material was stirred with 3.5M HCl for 1 hour (with 100 mL of acid, which also contained 25 mL of ethanol to ensure wetting), followed by washing with 100 mL of de-ionized water. The solid was collected by filtration. Acidification, washing and filtration were repeated a total of 5 times, and after the final wash the solid was dried under vacuum at 100° C. for 24 h. The illustrative example as described in Example 28 was carried out with the exception that 1 g of the material from this example was used in the catalysis run. The conversion was found to be 48% of heptene.

Example 48

$Me_2SiO/SiO_2$/"NAFION®" PFIEP Composite 20 g $Me_2Si(OMe)_2$ were mixed and 3 g of water and 0.3 g of 0.04M HCl was added and stirred for 5 min. To this solution 25 g of TMOS which was stirred with 0.3 g of 0.04M HCl and 3.5 g of water was added, and the silicon containing solution was stirred for 15 mins. To 50 g of the 5% "NAFION®" solution was added 25 mL of 0.4M NaOH over 1 min. Next the silicon containing solution was added to the stirred "NAFION®" solution, and the mixture was left to gel over about 30 seconds. The material was dried at 95° C. under a nitrogen flow. The hard glass-like product was ground and passed through a 10-mesh screen, and then the material was stirred with 3.5M HCl for 1 hour (with 100 mL of acid, which also contained 25 mL of ethanol to ensure wetting), followed by washing with 100 mL of de-ionized water. The solid was collected by filtration. Acidification, washing and filtration were repeated a total of 5 times and after the final wash the solid was dried under vacuum at 100° C. for 24 h. The illustrative example as described in Example 28 was carried out with the exception that 1 g of the material from this example was used in the catalysis run. The conversion was found to be 37% of heptene.

Example 49

Polydimethylsiloxane/Si/"NAFION®" PFIEP Composite 8 g of polydimethylsiloxane was added to 25 g of TMOS which was stirred with 0.3 g of 0.04M HCl and 3.5 g of water was added and the silicon containing solution was stirred for 15 mins. To 50 g of the 5% "NAFION®" solution was added 25 mL of 0.4M NaOH over 1 min. Next the silicon containing solution was added to the stirred "NAFION®" solution, and the mixture was left to gel over about 30 s. The material was dried at 95° C. under a nitrogen flow. The hard glass-like product was ground and passed through a 10-mesh screen, and then the material, was stirred with 3.5M HCl for 1 hour (with 100 mL of acid, which also contained 25 mL of ethanol to ensure wetting), followed by washing with 100 mL of de-ionized water. The solid was collected by filtration. Acidification, washing and filtration were repeated a total of 5 times, and after the final wash the solid was dried under vacuum at 100° C. for 24 h. The illustrative example as described in Example 28 was carried out with the exception that 1 g of the material from this example was used in the catalysis run. The conversion was found to be a 49% heptene.

Example 50

Comparative Example of "NAFION®" PFIEP Deposited Upon a Pre-Formed Support

Catalysis Study

A sample of "NAFION®" PFIEP deposited on top of a silica gel support was prepared according to the Illustrative Embodiment Ia of U.S. Pat. No. 4,038,213. The silica used was a porous silica (A Division silica 62). The surface area was 300 m²/g which is the same as described in U.S. Pat. No. 4,038,213, with a pore volume of 1.1 cc/gram. The porous silica support was treated with an alcohol solution of "NAFION®" (5% "NAFION®" PFIEP), and the alcohol was removed on a rotary evaporator leaving a 5% "NAFION®" on the silica catalyst. The support and "NAFION®" were dried at 150° C. before catalyst testing.

The illustrative example as described in Example 28 was carried out with the exception that 2 g of the material from Example 50 was used in the catalysis run. Thus, 2 g of a 5 wt. % "NAFION®" in silica was used, which had a total of 0.1 g of catalyst. The conversion was found to be 24% of heptene.

By comparison, when using the same "NAFION®" loading, using a "NAFION®" PFIEP/silica catalyst which had been made in situ (and consisted of highly dispersed and entrapped "NAFION®" PFIEP) as described, for example, in Examples 13–23 the conversion obtained was typically 85–99%. Thus, when 1 g of the material from Example 21 was used in the catalysis run (the the total weight of "NAFION®" PFIEP being 0.1 g), the conversion was found to be 86% of heptene.

Microscopy Study

The microscopy was performed using a Hitachi S-5000SP microscope (a scanning electron microscope available from Hitachi Instruments, Japan) with a Norum EDS x-ray analysis. Particles, prepared according to Example 21, about 1–2 mm in size were mounted in an epoxy resin, which was set and the resin and particles were polished to give a polished cross section of the particle, which reveals the interior of the particle. Using EDS x-ray analysis in a spot mode (which analyzes a small sub-micron area) showed the presence of Si, F, O and C all of which were present across the whole interior part of the particle. Several areas within a particle and several different particles were analyzed and in all cases wherever Si was detected, F was also detected showing the intimate mixture of the two. No areas enriched in entirely Si or entirely F were observed. A uniform distribution of Si and F was observed.

Particles prepared according to the Illustrative Embodiment Ia of U.S. Pat. No. 4,038,213 were in contrast non-uniform. In most of the sample where Si was detected, no measurable F was found. On the very edge of the silica, a band of material rich in F was found but no silica, representing a film of the "NAFION®" PFIEP on the outer edge of the silica particle, and not an intimate mixture of the "NAFION®" PFIEP. The film could be observed visibly and varied in thickness from about 0.1 to 4–5 microns on a particle of about 100 microns which showed no fluorine within it. The film (on the outer silica surface) was also absent in some areas. An intimate mixture of Si and was not observed.

Elemental x-ray maps (for Si, O and F) were prepared for the above two samples. Using the procedure as described in Example 21, a uniform distribution of all three elements was observed and was found within the entire particle of the microcomposite of the present invention.

An x-ray elemental map of the sample as prepared according to U.S. Pat. No. 4,038,213, showed a film of the fluorocarbon at the outer edge of the silica, with the bulk of the material being only silica.

Example 51

Catalytic Testing of "NAFION®" PFIEP/Silica Composites Using the Alkylation of Diphenyl Ether with Dodecene

ILLUSTRATIVE EXAMPLE OF THE PRESENT INVENTION

Both diphenyl ether and dodecene where dried over 3 A molecular sieve before use (dried for 24 hours). In a round bottom flask was added 17 g of diphenyl ether and 8.4 g of dodecene, and a "TEFLON®" coated magnetic stirrer added. A reflux condenser was attached to the flask and a slow stream of nitrogen passed over the top of the reflux condenser to minimize moisture. The flask and contents were heated to 150° C. A sample of 1 g of the "NAFION®" PFIEP/silica catalyst as described in Example 13 was dried in vacuum at 150° C. for 15 hours. The dried material was added to the diphenyl ether and dodecene mixture and the solution stirred and left to react for exactly 2 hours at 150° C. After two hours a sample was removed of the dodecene and was measured using gas chromatography. In the GC analysis dodecane was used as a standard. The conversion of diphenyl ether was measured to be greater than 99% leaving less than 1% of the dodecene unreacted.

Comparative Example

As a comparison experiment, the catalytic activity of 0.13 g of "NAFION®" NR50 was tested. 0.13 g represents the same weight of "NAFION®" PFIEP as tested above for the microcomposite. The exact same procedure was used, drying the NR50 at 150° C. for 16 hours and adding the NR50 to the stirred solution of dodecene (8.4 g) and diphenyl ether (17 g) at 150° C. After 2 hour reaction time the conversion was found to be about 5%, leaving 95% of the dodecene unreacted.

Example 52

60% "NAFION®" PFIEP in Silica

To 1200 g of a 5% "NAFION®" containing solution was added 150 g of 0.8M NaOH followed by 150 g of calcium carbonate powder. The flask and contents were ultrasonicated for 2 minutes using a sonic horn. Separately to 135 g of tetraethoxysilane was added 37 ml of water and 0.3 g of 3.5M HCl. The solution was stirred for 1 hour. The silica solution was added to the "NAFION®" containing solution and the mixture was left for 1 hour and then the material was dried in an oven at 95° C. for 2 days (with a stream of nitrogen purging through the oven), followed by drying in vacuum at 115° C. for 1 day. The solid was stirred with 1 liter of 3.5M HCl overnight, followed by washing with 500 ml of de-ionized water, and the solid collected by filtration. The solid was further stirred with 500 ml of 3.5M HCl for 1 hour, filtered and washed with 500 ml of de-ionized water and the process repeated a total of 5 times. After the final wash the solid was dried under vacuum at 100° C. for 24 h.

Acylation Reaction

Benzoyl chloride and m-xylene and were dried over a molecular sieve before use. In a round bottom flask was added 10.6 g of m-xylene and 7 g of benzoyl chloride, and a "TEFLON®" coated magnetic stirrer added. A reflux condenser was attached to the flask and a slow stream of nitrogen passed over the top of the reflux condenser to minimize moisture. The flask and contents were heated to 130° C. A sample of 0.17 gram of the "NAFION®" PFIEP/silica catalyst as described in this Example was dried in vacuum at 150° C. for 15 hours. The dried material was added to the m-xylene and benzoyl chloride mixture and the solution stirred and left to react for exactly 6 hours at 130° C. After six hours a sample was removed. In the GC analysis dodecane was used as a standard. The conversion of benzoyl chloride was found to be 75%.

Comparative Example

As a comparison experiment, the catalytic activity of 0.1 g of "NAFION®" NR50 PFIEP was tested. 0.1 g represents the same weight of "NAFION®" PFIEP as tested above for the composite. The exact same procedure was used, drying the "NAFION®" NR50 PFIEP at 150° C. for 16 hours and adding the "NAFION®" NR50 PFIEP to the stirred solution of m-xylene and benzoyl chloride at 130° C. After 6 hour reaction time the conversion was found to be about 17%.

Example 53

The catalyst as prepared in Example 45 was used in this Example for catalytic testing of "NAFION®" PFIEP/silica composites using the acylation of m-xylene with benzoyl chloride.

The m-xylene and benzoyl chloride were dried over molecular sieve before use. In a round bottom flask was added 10.6 g of m-xylene and 7 g of benzoyl chloride, and a "TEFLON®" coated magnetic stirrer added. A reflux condenser was attached to the flask and a slow stream of nitrogen passed over the top of the reflux condenser to minimize moisture. The flask and contents were heated to 130° C. The "NAFION®" PFIEP/silica composition (about 5 grams) was ground to a fine powder using a mortar and pestle over about 10 minutes. A sample of 0.125 gram of the "NAFION®" PFIEP/silica catalyst as described in Example 45 was dried in vacuum at 150° C. for 15 hours. The dried material was added to the m-xylene and benzoyl chloride mixture and the solution stirred and left to react for exactly 6 hours at 130° C. After six hours a sample was removed. In the GC analysis dodecane was used as a standard. The conversion of benzoyl chloride was found to be 90%, as compared to a conversion of 17% for the comparative example as described above in the Comparative Example of 52.

Example 54

40% "NAFION®" PFIEP in Silica

To 1200 ml of "NAFION®" was added 150 ml of 1.2M NaOH over about 10 minutes. Separately 204 g of tetramethoxysilane, 32.6 g of water and 3 g of 0.04M HCl were mixed for 45 minutes and the silicon containing solution was added to the "NAFION®" containing solution. The solution gelled in about 1 minute and the flask and contents were placed in an oven at 100° C., with a nitrogen flow, for 2 days, followed by vacuum drying for an additional day. The solid was ground and passed through a 10 mesh screen and the solid was stirred with 3.5M HCl for 1 hour (with 500 ml of acid), followed by washing with 500 ml of de-ionzied water, and the solid collected by filtration. This process was repeated a total of 5 times and after the final wash the solid was dried under vacuum at 100° C. for 24 h.

Acylation Reaction

The m-xylene and benzoyl chloride were dried over molecular sieve before use. In a round bottom flask was added 10.6 g of m-xylene and 7 g of benzoyl chloride, and a "TEFLON®" coated magnetic stirrer added. A reflux condenser was attached to the flask and a slow stream of nitrogen passed over the top of the reflux condenser to minimize moisture. The flask and contents were heated to 130° C. A sample of 0.25 g of the "NAFION®" PFIEP/silica catalyst as described in this Example was dried in vacuum at 150° C. for 15 hours. The dried material was added to the m-xylene and benzoyl chloride mixture and the solution stirred and left to react for exactly 6 hours at 130° C. After six hours a sample was removed. In the GC analysis dodecane was used as a standard. The conversion of benzoyl chloride was found to be 68% as compared to a conversion of 17% for the Comparative Example as described above in the Comparative Example 52.

Example 55

To 350 ml of a 5% "NAFION®" containing solution was added 7.5 g of 8M NaOH. The solution was stirred for about 2 minutes. Separately, 12 ml of water and 1 ml of 0.04M HCl were added to 75 g of tetramethoxysilane. The solution was stirred for 45 minutes, and the silicon containing solution was added to the "NAFION®" solution. The system gelled in about 10 seconds and the flask and contents were dried in an oven at 95° C. for 2 days followed by drying in vacuum at 117° C. for a further day. The solid was ground and passed through a 10-mesh screen, and then the material was stirred with 3.5M HCl for 1 hour (with 250 ml of acid), followed by washing with 100 ml of de-ionized water, and the solid collected by filtration. This process was repeated a total of times, and after the final wash (with 1000 ml of de-ionized water) the solid was dried under vacuum at 100° C. for 24 h.

Example 56

To 175 ml of a 5% "NAFION®" containing solution was added 2.5 g of 8M NaOH. The solution was stirred for about 2 minutes. Separately, 6 ml of water and 0.6 ml of 0.04M HCl were added to 42 g of tetramethoxysilane. The solution was stirred for 5 minutes and then added to the "NAFION®" solution. The system gelled in about 10 seconds and the flask and contents were dried in an oven at 95° C. for 2 days followed by drying in vacuum at 117° C. for a further day. The solid was ground and passed through a 10-mesh screen, and then the material was stirred with 3.5M HCl for 1 hour (with 250 ml of acid), followed by washing with 100 ml of de-ionized water, and the solid collected by filtration. This process was repeated a total of 5 times, and after the final wash (with 1000 ml of de-ionized water) the solid was dried under vacuum at 100° C. for 24 h.

Example 57

1-Butene Isomerization in the Gas Phase

Solid acid catalyzed 1-butene isomerization to cis-2-butene, trans-2-butene and isobutene was carried out at temperatures between 50-250° C. and ambient pressure in a ½" stainless steel reactor. The tested acid catalyst of the present invention was the 13 wt % "NAFION®" PFIEP/silica microcomposite prepared in Example 16 which was compared with "NAFION®" NR50 and "AMBERLYST 15®". Typically, between 2.5–5.0 g of catalyst were loaded in the reactor. Prior to the reaction, catalysts were dried in vacuum oven at 150° C. for overnight except "AMBERLYST 150" was dried at 110° C. The reactant 1-butene was diluted with helium. The reaction mixture was analyzed by on-line gas chromatography (GC) equipped with a Flame Ionization Detector (FID) and a 25 m Plot column coated with $Al_2O_3/KCl$.

The 1-butene isomerization results over the 2.5 g of the 13 wt % "NAFION®" PFIEP/silica microcomposite catalyst of the present invention are listed in Table 1a and Table 1b below. Data in Table 1a show that the microcomposite prepared as in Example 16 is very efficient for the title reaction under mild conditions, even at 50° C., significant amount of 1-butene were converted to the 2-butenes. At 100° C., near equilibrium n-butene distribution was obtained and extremely small amounts of isobutene were formed. Isobutene as well as oligomers formed over the microcomposite catalyst were less than that produced from the "NAFION®" NR50 beads catalyst (see Table 2a below).

TABLE 1a

Product Distribution for 1-Butene Isomerization over 2.5 g 13 wt % "NAFION®" PFIEP/Silica Microcomposite Catalyst Under Ambient Pressure with Flow Rate of He = 1-Butene = 38 ml/min, WHSV of 1-Butene = 2 $hr^{-1}$

| % Butenes | Temperature (° C.) | | | | |
|---|---|---|---|---|---|
| | 50 | 100 | 150 | 200 | 250 |
| 1-butene | 38.0 | 15.8 | 15.3 | 21.2 | 25.0 |
| trans-2-butene | 33.9 | 54.9 | 5.4 | 45.6 | 42.4 |
| cis-2-butene | 28.1 | 29.3 | 31.0 | 31.8 | 31.9 |
| isobutene | — | — | 0.3 | 0.4 | 0.7 |
| Oligomers | — | — | — | ~2% | ~5% |

The reactant flow rate effect on the isomerziation over the microcomposite was studied and the results are shown in Table 1b below. At 50° C., the thermodynamic equilibrium distribution of n-butenes is 4.1%, 70.5%, and 25.4% for 1-butene, trans-2-butene, and cis-2-butene, respectively. Data in Table 1b indicate that the equilibrium distribution of n-butene can be readily obtained over the microcomposite catalyst at temperatures as low as 50° C.

TABLE 1b

Product Distribution for 1-Butene Isomerization over 2.5 g 13 wt % "NAFION®" PFIEP/Silica Composite Catalyst Under Ambient Pressure at 50° C. and Different WHSV of 1-Butene with Flow Ratio of He/1-Butene = 2/1

| % Butenes | WHSV ($hr^{-1}$) | | |
|---|---|---|---|
| | 0.4 | 0.8 | 1.6 |
| 1-butene | 6.9 | 14.9 | 37.8 |
| trans-2-butene | 66.3 | 56.2 | 34.6 |
| cis-2-butene | 26.8 | 28.9 | 27.6 |
| isobutene | — | — | — |

Comparison with "NAFION®" NR50

Table 2a below lists the results from 1-butene isomerization over the "NAFION®" NR50 beads at different temperatures. At 50° C. and the other reaction conditions listed in Table 2a, 1-butene conversion was less than 1%. 1-Butene conversion increased gradually with increased reaction temperature up to 200° C. The "NAFION®" NR50 beads melted at 250° C. and resulted in decreased activity. At the temperature where "NAFION®" NR50 could effectively catalyze the 1-butene isomerization, about 200° C., significant amount of oligomers of butene ($C_8$+hydrocarbons) and the cracking products of those oligomers ($C_1$–$C_7$ hydrocarbons) were also formed. In all cases, isobutene formation was negligible.

TABLE 2a

Product Distribtion for 1-Butene Isomerization over 5.0 g "NAFION®" NR50 Catalyst Under Ambient Pressure with Flow Rate of He = 1-butene = 38 ml/min, WHSV of 1-butene = 1 $hr^{-1}$

| % Butenes | Temperature (° C.) | | | | |
|---|---|---|---|---|---|
| | 50 | 100 | 150 | 200 | 250 |
| 1-butene | >99.0 | 86.1 | 38.1 | 18.6 | 24.1 |
| trans-2-butene | — | 5.8 | 36.0 | 48.1 | 42.9 |
| cis-2-butene | <1.0 | 8.0 | 25.7 | 31.6 | 31.0 |
| isobutene | — | 0.1 | 0.2 | 1.7 | 3.0 |
| Oligomers | — | — | ~9% | ~27% | ~36% |

The effect of reactant flow rate, that is the weight hourly space velocity (WHSV) of butene ($hr^{-1}$) was investigated and the result obtained at 150° C. was listed in Table 2b below. As the flow rate was decreased, the contact times of the reactant with solid catalyst increased, and consequently the 1-butene conversion to 2-butenes increased. However, the thermodynamic equilibrium distribution of butenes were not reached over the "NAFION®" NR50 catalyst under the reaction conditions employed. Only small changes of 1-butene were realized when the same study was carried out at 100° C. and almost no effect of WHSV on 1-butene conversion was seen at 50° C.

TABLE 2b

Product Distribution for 1-Butene Isomerization over 5.0 g "NAFION®" NR50 Catalyst Under Ambient Pressure at 150° C. and Different WHSV of 1-Butene with Flow Ratio of He/1-Butene = 2/1

| % Butenes | WHSV ($hr^{-1}$) | | |
|---|---|---|---|
| | 0.2 | 0.4 | 0.8 |
| 1-butene | 18.1 | 32.9 | 42.2 |
| trans-2-butene | 51.2 | 40.8 | 34.8 |
| cis-2-butene | 30.2 | 26.0 | 23.0 |
| isobutene | 0.5 | 0.3 | — |
| Oligomers | 25% | 12% | 9% |

Comparison with "AMBERLYST 15®"

1-Butene isomerization over commercial "AMBERLYST 15®" resin catalyst was also carried out under similar conditions for comparison. The temperature and flow rate effects are shown below in Table 3a and Table 3b, respectively. The highest temperature studied was 100° C. because the "AMBERLYST 15®" is known to decompose and lose sulfonic groups at elevated temperatures (>130° C.). Data in Table 3a show that the macroporous "AMBERLYST 15®" catalyst (surface area 34 $m^2/g$) is an effective catalyst for the 1-butene isomerization to the linear 2-butenes at the conditions employed and near equilibrium n-butene distribution was obtained at 100° C. Similar to the results obtained from the "NAFION®" NR50 and "NAFION®" PFIEP/silica microcomposite catalysts, isobutene formation was negligible in all cases.

TABLE 3a

Product Distribution for 1-Butene Isomerization over 5.0 g "AMBERLYST 15 ®" Catalyst Under Ambient Pressure with Flow Rate of He = 110 ml/min and 1-Butene = 90 ml/min, WHSV of 1-Butene = 2.5 hr$^{-1}$

| % Butenes | Temperature (° C.) | | |
|---|---|---|---|
| | 50 | 75 | 100 |
| 1-butene | 69.8 | 10.7 | 8.2 |
| trans-2-butene | 17.1 | 62.2 | 62.8 |
| cis-2-butene | 13.1 | 27.1 | 28.8 |
| isobutene | — | — | 0.2 |
| Oligomers | — | 1.5% | 4.0% |

Equilibrium was not reached at 50° C. even when very low flow rate of 1-butene was used (Table 3b).

TABLE 3b

Product Distribution for 1-Butene Isomerization over 5.0 g "AMBERLYST 15 ®" Catalyst Under Ambient Pressure at 50° C. and Different WHSV of 1-Butene with Flow Ratio of He/1-Butene = 1.2/1.0

| % Butenes | WHSV (hr − 1) | | | | |
|---|---|---|---|---|---|
| | 0.28 | 0.44 | 1.03 | 2.08 | 2.50 |
| 1-butene | 24.7 | 31.0 | 53.0 | 67.8 | 69.8 |
| trans-2-butene | 51.2 | 46.2 | 29.3 | 19.2 | 17.1 |
| cis-2-butene | 24.1 | 22.8 | 17.7 | 13.0 | 13.1 |
| isobutene | — | — | — | — | — |

Example 58

1-Butene Isomerization in the Gas Phase

Solid acid catalyzed 1-butene isomerization to cis-2-butene, trans-2-butene and isobutene was carried out at temperatures between 23-250° C. and ambient pressure with a ½" stainless steel reactor. A 13 wt % "NAFION®" PFIEP/silica microcomposite as prepared in Example 16 was dried at 150° C. overnight. The reactant 1-butene was diluted with helium. The reaction mixture was analyzed by an on-line GC equipped with a FID detector and a 25 m Plot column coated with $Al_2O_3$/KCl.

The 1-butene isomerization results over the 13 wt % "NAFION®" PFIEP/silica microcomposite catalyst are shown in Tables 4a and 4b below. FIG. 1 is a graph showing the data from Table 4b plotting the reciprocal of WHSV.

TABLE 4a

Product Distribution for 1-Butene Isomerization over 5.0 g 13 wt % "NAFION ®" PFIEP/Silica Microcomposite Catalyst Under Ambient Pressure with Flow Rate of He = 105 ml/min and 1-Butene = 6 ml/min, WHSV of 1-Butene = 0.16 hr$^{-1}$

| % Butenes | Temperature (° C.) | | | | |
|---|---|---|---|---|---|
| | 50 | 100 | 150 | 200 | 250 |
| 1-butene | 10.3 | 7.8 | 10.5 | 23.0 | 16.1 |
| trans-2-butene | 62.4 | 63.2 | 57.9 | 54.6 | 50.8 |
| cis-2-butene | 27.3 | 28.6 | 29.9 | 29.9 | 31.2 |
| isobutene | — | 0.1 | 0.4 | 1.1 | 1.5 |
| Oligomers | <1% | 3% | 3% | 3% | 3% |

TABLE 4b

Product Distribution for 1-Butene Isomerization over 5.0 g 13 wt. % "NAFION ®" PFIEP/Silica Microcomposite Catalyst Under Ambient Pressure at 50° C. and Different WHSV of 1-Butene with Flow Ratio of He/1-Butene = 1.21/1

| % Butenes | WHSV (hr$^{-1}$) | | |
|---|---|---|---|
| | 1.0 | 1.6 | 2.5 |
| 1-butene | 6.6 | 8.8 | 9.2 |
| trans-2-butene | 66.9 | 64.0 | 63.6 |
| cis-2-butene | 26.5 | 27.2 | 27.2 |
| isobutene | — | — | — |

Example 59

1-Heptene Isomerization in the Liquid Phase

Solid acid catalyzed 1-heptene isomerization to 2- and 3-heptenes (including cis- and trans-isomers of each) were carried out in the liquid phase at 60° C. Typically, 10 g of 1-heptene, 30 g of n-hexane and 2 g of solid catalyst which was predried were charged to a two-neck flask with a magnetic stir bar for mixing. n-Hexane served as solvent for the reaction and internal standard for the GC analysis. Liquid samples were taken at certain time intervals and analyzed by the GC that was described earlier. All of the five isomers were separated and identified. Good material balances were obtained and formation of oligomers was negligible. The 1-heptene conversions after 1 hr at 60° C. and the first order rate constants that were calculated from the data at low 1-heptene conversions (<15%) are listed in Table 5 below. Similar to the gas phase 1-butene isomerization, the 13 wt % "NAFION®" PFIEP/silica microcomposite as prepared in Example 16 was significantly more active than the "NAFION®" NR50 beads and also was about 6 times more active than the "AMBERLYST 15®" catalyst based on the unit weight of the solid catalyst.

TABLE 5

1-Heptene Conversion (mol %) after 1 hr at 60° C. and the First Order Rate Constant for 1-Heptene Isomerization over 2 g of Solid Acid Catalysts

| Catalyst | 13 wt % "NAFION ®" PFIEP/Silica Microcomposite | "NAFION ®" NR50 | "AMBERLYST 15 ®" |
|---|---|---|---|
| 1-Heptene Conv. (%) | 86.4 | 3.8 | 20.6 |
| Rate Constant (mM/gcat · hr) | 86.8 | 2.0 | 13.7 |

Example 60

1-Dodecene Isomerization in the Liquid Phase

1-Dodecene isomerization to its isomers was carried out in the liquid phase at 75° C. over 13 wt % "NAFION®" PFIEP/silica microcomposite as prepared in Example 16 and compared with "NAFION®" NR50 and "AMBERLYST 15®" catalysts. For a typical run, 10 g of 1-dodecene, 30 g of cyclohexane and 2 g of solid catalyst which was predried were charged to a two-neck flask with a magnetic stir bar for mixing. Cyclohexane served as solvent for the reaction and internal standard for the GC analysis. Liquid samples were taken at certain time intervals and analyzed by the GC that was described earlier. There was no attempt to identify all of the n-dodecene isomers and only the 1-dodecene conversion was monitored by following the decreasing of its GC peak area. Formation of oligomers was negligible. The 1-dodecene conversions after 1 hr at 75° C. and the first order rate constants that were calculated from the data at low 1-dodecene conversions (<15%) were listed in Table 6 below. Similar to the gas phase 1-butene isomerization and the liquid phase 1-heptene isomerization, the 13 wt % "NAFION®" PFIEP/silica microcomposite was the most active catalyst which was about 20 times more active than the "NAFION®" NR50 beads and was also about 4 times more active than the "AMBERLYST 15®" catalyst based on the unit weight of the solid catlayst.

TABLE 6

1-Dodecene Conversion (mol %) After 1 hr at 75° C. and the First Order Rate Constant for 1-Dodecene Isomerization over 2 g of Solid Acid Catalysts

| Catalyst | 13 wt % "NAFION ®" PFIEP/Silica Microcomposite | "NAFION ®" NR50 | "AMBERLYST 15 ®" |
|---|---|---|---|
| 1-Dodecene Conv. (%) | 76.6 | 13.6 | 57.7 |
| Rate Constant (mM/gcat · hr) | 192.5 | 9.2 | 52.2 |

What is claimed is:

1. An improved process for the esterification of a carboxylic acid with an olefin wherein the improvement comprises contacting said carboxylic acid with a catalytic porous microcomposite comprising perfluorinated ion-exchange polymer with pendant sulfonic and/or carboxylic acid groups entrapped within and highly dispersed throughout a network of metal oxide, wherein the weight percentage of perfluorinated ion-exchange polymer in the microcomposite is from about 0.1 to about 90 percent, and wherein the size of the pores in the microcomposite is about 0.5 nm to about 75 nm.

2. The process of claim 1 wherein the carboxylic acid is acetic acid and the olefin is cyclohexene.

3. The process of claim 1 wherein the perfluorinated ion-exchange polymer contains pendant sulfonic acid groups and the metal oxide is silica, alumina, titania, germania, zirconia, alumino-silicate, zirconyl-silicate, chromic oxide and/or iron oxide.

4. The process of claim 3 wherein the metal oxide is silica.

5. The process of claim 1 wherein the microcomposite further comprises pores having a size in the range of about 75 nm to about 1000 nm.

6. The process of claim 4 wherein the perfluorinated ion-exchange polymer has about 6.3 tetrafluoroethylene molecules for every perfluoro(3,6-dioxa-4-methyl-7-octenesulfonyl fluoride) molecule and has an equivalent weight of about 1070.

* * * * *